US009568506B2

(12) United States Patent
Fujinoki

(10) Patent No.: US 9,568,506 B2
(45) Date of Patent: Feb. 14, 2017

(54) ELECTRIC FIELD MEASUREMENT DEVICE

(71) Applicant: Panasonic Intellectual Property Management Co., Ltd., Osaka (JP)

(72) Inventor: Norihito Fujinoki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 170 days.

(21) Appl. No.: 14/406,896

(22) PCT Filed: May 15, 2014

(86) PCT No.: PCT/JP2014/002572
§ 371 (c)(1),
(2) Date: Dec. 10, 2014

(87) PCT Pub. No.: WO2014/188685
PCT Pub. Date: Nov. 27, 2014

(65) Prior Publication Data
US 2015/0185256 A1 Jul. 2, 2015

(30) Foreign Application Priority Data
May 22, 2013 (JP) ................................. 2013-107715

(51) Int. Cl.
G01R 15/24 (2006.01)
H04B 13/00 (2006.01)
(Continued)

(52) U.S. Cl.
CPC ........... *G01R 15/241* (2013.01); *A61B 5/0059* (2013.01); *A61B 5/0476* (2013.01); *G02F 1/035* (2013.01);
(Continued)

(58) Field of Classification Search
CPC ...... G01R 15/241; G01R 15/246; G01R 1/071
See application file for complete search history.

(56) References Cited

U.S. PATENT DOCUMENTS 4,989,190 A * 1/1991 Kuroe ................ G11B 7/08541
358/907
5,210,407 A * 5/1993 Ito ........................... G01R 29/12
250/227.11
(Continued)

FOREIGN PATENT DOCUMENTS

JP 6-109785 4/1994
JP 7-151804 6/1995
(Continued)

OTHER PUBLICATIONS

International Search Report issued Aug. 12, 2014 in International (PCT) Application No. PCT/JP2014/002572.

*Primary Examiner* — Huy Q Phan
*Assistant Examiner* — Alvaro Fortich
(74) *Attorney, Agent, or Firm* — Wenderoth, Lind & Ponack, L.L.P.

(57) ABSTRACT

The present application discloses electric field measurement device for measuring electric field of a target. Electric field measurement device includes optical waveguide which transmits transmission light, electrode portion, which gives optical characteristics of optical waveguide periodic variation, antenna for setting first state, in which electric field is coupled to optical waveguide, and second state, in which electric field is disconnected from optical waveguide, detector which detects light intensity of emission light emitted from optical waveguide, and applicator which applies voltage to electrode portion to give periodic variation. Applicator includes setting portion, which sets reference voltage in correspondence to light intensity under the second state, and output portion, which outputs voltage in correspondence to (Continued)

difference between reference voltage and induced voltage happening to electrode portion under first state.

14 Claims, 17 Drawing Sheets

(51) Int. Cl.
  *A61B 5/00* (2006.01)
  *A61B 5/0476* (2006.01)
  *G02F 1/035* (2006.01)
  *G01R 29/08* (2006.01)
(52) U.S. Cl.
  CPC ..... H04B 13/005 (2013.01); *A61B 2562/0233* (2013.01); *G01R 29/0885* (2013.01)

(56) References Cited

U.S. PATENT DOCUMENTS

| | | | | |
|---|---|---|---|---|
| 5,781,003 A | * | 7/1998 | Kondo | G01R 15/241 324/96 |
| 5,850,140 A | * | 12/1998 | Tokano | G01R 29/0885 324/96 |
| 5,907,426 A | * | 5/1999 | Kato | G01D 3/028 359/239 |
| 6,487,352 B1 | * | 11/2002 | Sobiski | H04B 10/25133 359/337.5 |
| 2004/0094698 A1 | * | 5/2004 | Imaki | G01J 9/00 250/225 |
| 2007/0147724 A1 | * | 6/2007 | Ishizaka | G02F 1/0147 385/8 |
| 2007/0264029 A1 | * | 11/2007 | Suzuki | H04B 10/66 398/188 |
| 2008/0144989 A1 | * | 6/2008 | Sakurai | G02F 1/3132 385/3 |
| 2009/0185459 A1 | * | 7/2009 | Matsumoto | G11B 5/4826 369/13.02 |
| 2010/0308428 A1 | * | 12/2010 | Okamoto | H01L 31/03529 257/432 |

FOREIGN PATENT DOCUMENTS

| | | |
|---|---|---|
| JP | 9-113557 | 5/1997 |
| JP | 11-194146 | 7/1999 |
| JP | 2002-122622 | 4/2002 |
| JP | 2003-98205 | 4/2003 |

* cited by examiner

ELECTRIC FIELD MEASUREMENT DEVICE

TECHNICAL FIELD

The present invention relates to an electric field measurement device for measuring an electric field.

BACKGROUND ART

An electric field measurement device detects an electric field and generates electrical signals representing intensity of the electric field. The electric field measurement device may be used for various applications. For example, an electric field measurement device may be utilized as a human body communication device which performs data communication between wearable computers. An electric field measurement device may be utilized as a basic element of an electroencephalograph, which measures brain activity of a subject such as a human or animal, or another measurement device, which detects biological processes. The electric field measurement device utilized as an electroencephalograph may be situated outside the body of a subject to detect a resultant variation in an electric field from brain activity. It may be important qualities for these applications that the electric field measurement device has high sensitivity, a small size and high resistance to impact.

An electric field measurement device may include an electro-optic crystal. The electric field measurement device applies an electric field to the electro-optic crystal to induce an electro-optic (EO) effect. The electric field measurement device may use the electro-optic effect to detect an electric field in a non-contact manner.

As a result of the electro-optic effect, there is a change in optical characteristics of the electro-optic crystal such as a refractive index. A user using the electric field measurement device changes the refractive index of the electro-optic crystal and causes light to enter the electro-optic crystal. A phase of the light is changed in the electro-optic crystal. A change in intensity or phase of emission light emitted from the electro-optic crystal is electrically detected.

The electric field measurement device utilizing the electro-optic effect optically transmits detection signals representing a detected electric field. Therefore, the detection signals are less susceptible to induction or electrical noise. Since the electro-optic effect of the electro-optic crystal is utilized, the electric field measurement device may be responsive. In addition, the electric field measurement device may transmit the detection signals with little loss.

A resultant change in refractive index from the electro-optic effect is slight. Therefore, some of conventional electric field measurement devices, which use the electro-optic effect, utilize a phase change in light entering a non-linear optical crystal with the electro-optic effect. Other conventional electric field measurement devices may utilize an interferometer to improve sensitivity (c.f. Patent Documents 1 to 3).

Conventional electric field measurement devices are likely to be susceptible to environmental changes. Or, it is required that complex structures are incorporated into a conventional electric field measurement device in order to make the conventional electric field measurement device less susceptible to environmental changes.

Patent Document 1: JP 2003-98205 A
Patent Document 2: JP H07-151804 A
Patent Document 3: JP H11-194146 A

SUMMARY OF INVENTION

An object of the present invention is to provide a structurally simplified electric field measurement device configured to detect an electric field accurately even under environmental changes.

An electric field measurement device according to one aspect of the present invention measures an electric field of a measurement target. The electric field measurement device includes an optical waveguide configured to transmit transmission light, an electrode portion configured to give optical characteristics of the optical waveguide a periodic variation, an antenna configured to set a first state, in which the electric field is coupled to the optical waveguide, and a second state, in which the electric field is disconnected from the optical waveguide, a detector configured to detect light intensity of emission light emitted from the optical waveguide, and an applicator which applies a voltage to the electrode portion to give the periodic variation. The applicator includes a setting portion, which sets a reference voltage in correspondence to the light intensity under the second state, and an output portion, which outputs a voltage in correspondence to a difference between the reference voltage and an induced voltage happening to the electrode portion under the first state.

The aforementioned electric field measurement with a simple structure may detect an electric field accurately even under environmental changes.

The object, feature, and advantage of the present invention will become clearer with the detailed description below and the accompanying drawings.

DESCRIPTION OF EMBODIMENTS

Figure 1:
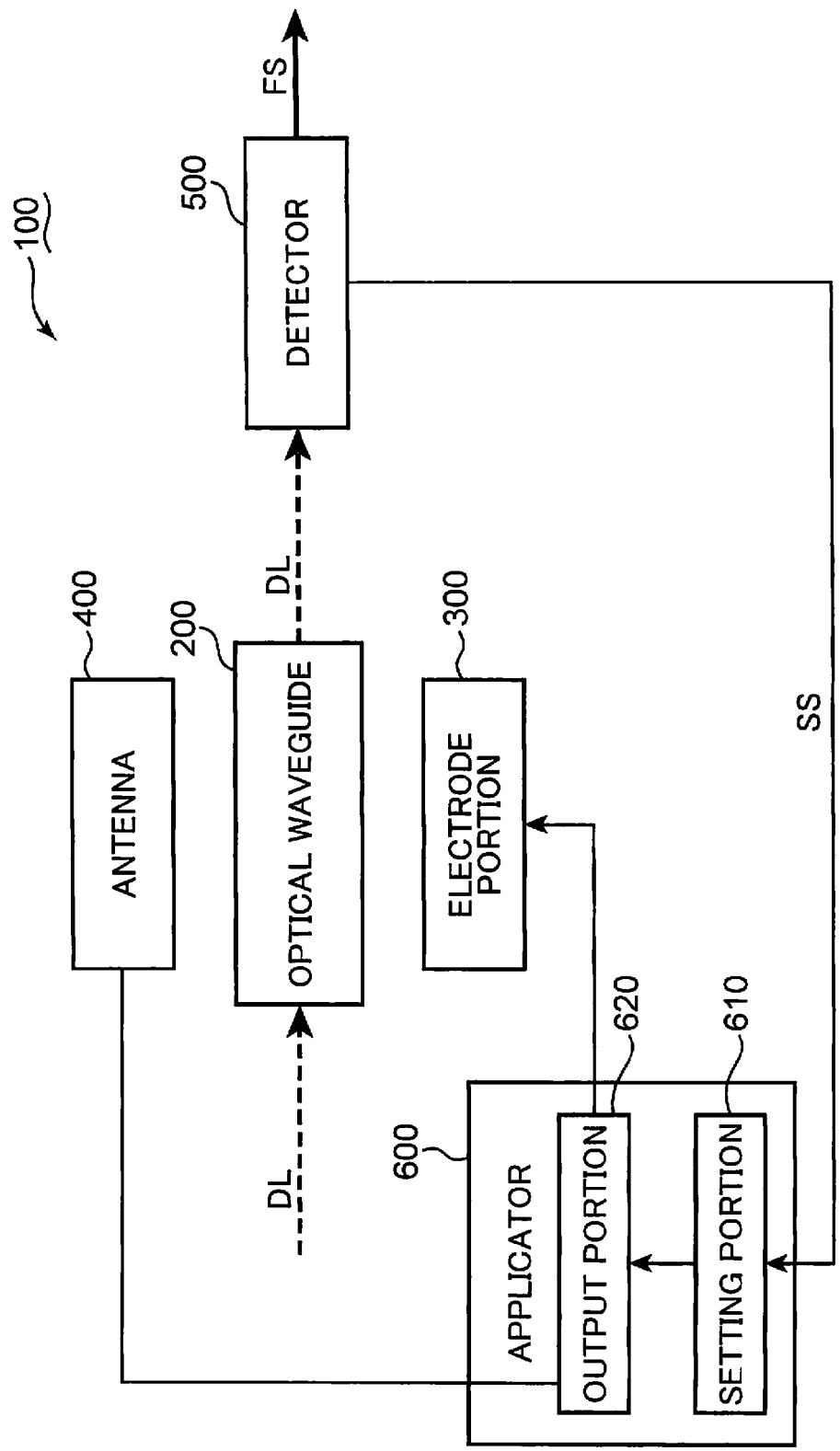
FIG. 1 is a schematic view of an electric field measurement device according to the first embodiment.

Various embodiments of exemplary electric field measurement devices are described with reference to the drawings. In the following embodiments, the same components are denoted by the same reference signs. For explanatory clarity, redundant description is omitted. Configurations, arrangements or shapes shown in the drawing and descriptions about the drawing are merely for the purpose of making principles of the embodiments easily understood. Therefore, the principles of the following embodiments are not limited by these in any way. Directional terms such as "up", "down", "left" or "right" are merely for the purpose of explanatory clarity. Accordingly, these terms should not be interpreted restrictively.

<Problem of Conventional Techniques Found by Present Inventors>

The present inventors studied conventional electric field detection techniques and found various problems. The electric field measurement devices described below in the context of the various embodiments have been developed to solve these problems.

(Problems of Electric Field Detection Techniques of Patent Document 1)

Figure 15:
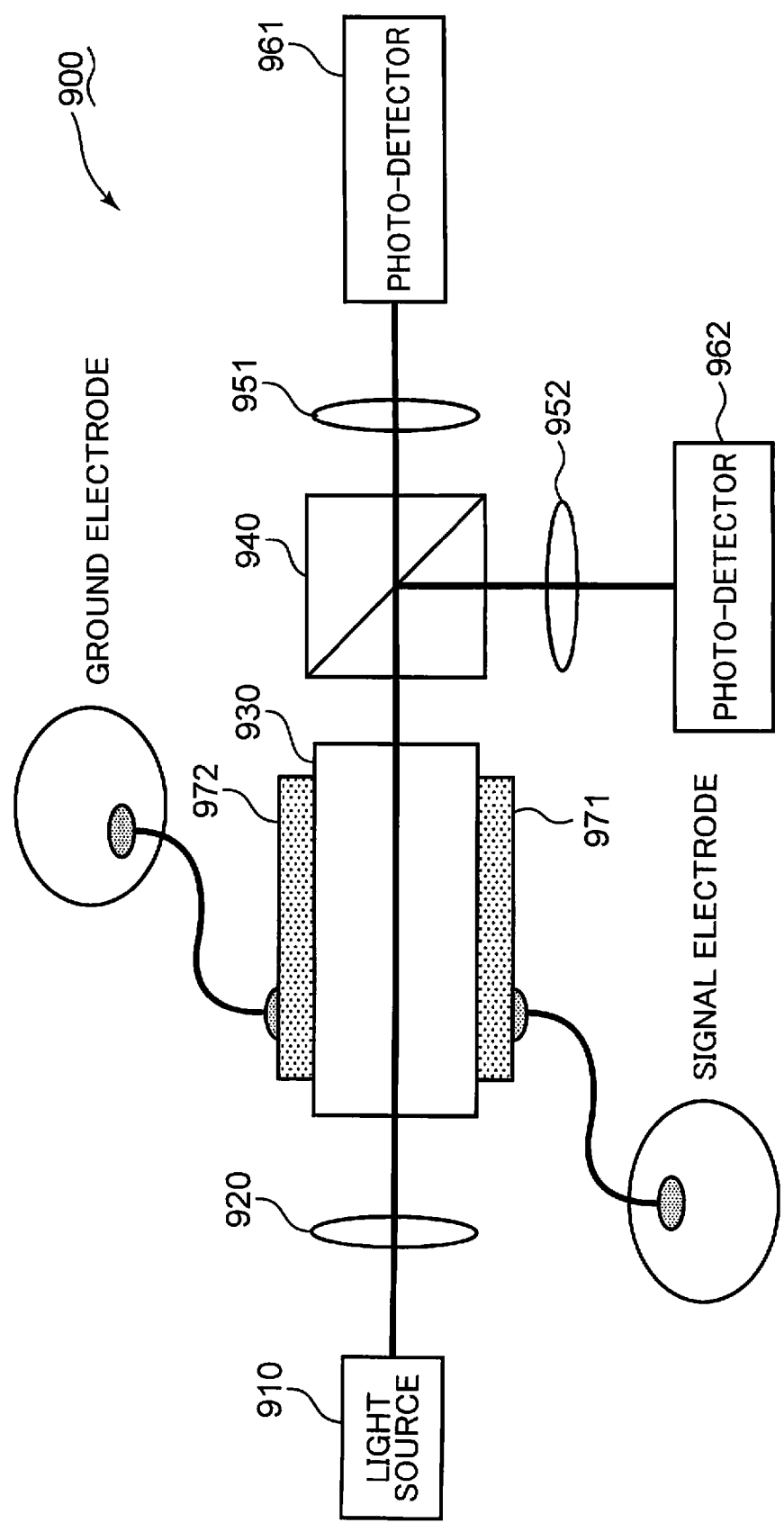
FIG. 15 is a schematic view of an electric field measurement device in Patent Document 1.

FIG. 15 is a schematic view of the electric field measurement device 900 of Patent Document 1. Problems of the electric field measurement device 900 of Patent Document 1 are described with reference to FIG. 15.

The electric field measurement device 900 includes a light source 910, a collimating lens 920, an electro-optic crystal 930, a polarization beam splitter 940, collecting lenses 951, 952, photo-detectors 961, 962, a signal electrode 971 and a ground electrode 972. An electric field of a measurement target (not shown) is coupled to the electro-optic crystal 930 through the signal electrode 971. Consequently, optical characteristics of the electro-optic crystal 930 changes substantially evenly over a propagation path of laser light emitted from the light source 910.

After the change in the optical characteristics, the light source 910 emits laser light toward the collimating lens 920. The collimating lens 920 forms collimated light from the laser light. Then, the laser light enters the electro-optic crystal 930.

The electro-optic crystal 930 changes a polarization condition of the laser light. The laser light is then emitted from the electro-optic crystal 930 to the polarization beam splitter 940. The polarization beam splitter 940 splits the laser light into a P-wave and an S-wave. The P-wave reaches the photo-detector 961 through the collecting lens 951. The S-wave reaches the photo-detector 962 through the collecting lens 952.

The photo-detector 961 outputs electrical signals in correspondence to light intensity of the P-wave. The photo-detector 962 outputs electrical signals in correspondence to light intensity of the S-wave. The electric field measurement device 900 analyzes the electrical signals to measure an electric field of the measurement target.

Intensity of laser light emitted from the electro-optic crystal 930 is likely to be affected by a change in temperature around the electric field measurement device 900. Therefore, the electric field measurement device 900 may not measure an electric field with high sensitivity.

An amount of phase change between before and after a change in optical characteristics of the electro-optic crystal 930 is very small. Therefore, amplitude of the electrical signals generated by the photo-detectors 961, 962 is very small. In order for the photo-detectors 961, 962 to generate electrical signals with large amplitude, the electro-optic crystal 930 have to have a long dimension in the propagating direction of the laser light. Accordingly, a designer gives the electric field measurement device 900 a large dimension. If a large crystal with high-quality is utilized as the electro-optic crystal 930, a manufacturing cost of the electric field measurement device 900 becomes very high.

(Problems of Electric Field Detection Techniques of Patent Document 2)

Figure 16:
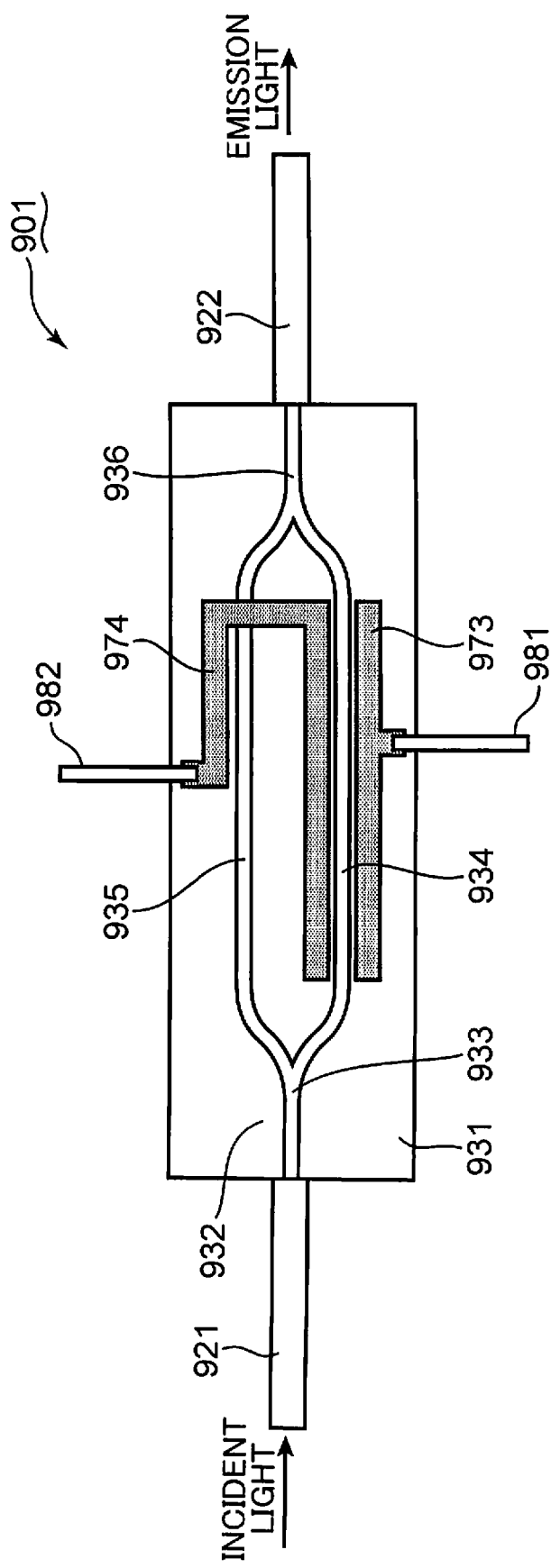
FIG. 16 is a schematic view of an electric field measurement device in Patent Document 2.

FIG. 16 is a schematic view of the electric field measurement device 901 of Patent Document 2. Problems of the electric field measurement device 901 of Patent Document 2 are described with reference to FIG. 16.

The electric field measurement device 901 includes a substrate 931 and an optical waveguide 932. The substrate 931 is formed from an electro-optic crystal. The optical waveguide 932 is formed on the substrate 931. The optical waveguide 932 includes an upstream waveguide 933, branched waveguides 934, 935 and a downstream waveguide 936. The substrate 931 and the optical waveguide 932 form a Mach-Zehnder interferometer.

The electric field measurement device 901 includes optical fibers 921, 922, electrodes 973, 974, and antennas 981, 982. Light propagates to the upstream waveguide 933 through the optical fiber 921. The light is then divided into light propagating along the branched waveguide 934 and light propagating along the branched waveguide 935. The light propagating along the branched waveguide 934 and the light propagating along the branched waveguide 935 are not different in light intensity. The light propagating along the branched waveguide 934 and the light propagating along the branched waveguide 935 then converge at the downstream waveguide 936 to be emitted toward a photo-detector (not shown) through the optical fiber 922.

The branched waveguide 934 extends between the electrodes 973, 974. The antenna 981 is connected to the electrode 973. The antenna 982 is connected to the electrode 974. An electric field of a measurement target is applied to the branched waveguide 934 through the antennas 981, 982 and the electrodes 973, 974. Consequently, there is a change in refractive index of the branched waveguide 934. As a result of the change in refractive index of the branched waveguide 934, a difference in optical path length between the branched waveguides 934, 935 also changes. A photo-detector outputs electrical signals representing the change in the difference in optical path length. Consequently, the electric field measurement device 901 may measure an electric field of the measurement target. Like the techniques of Patent Document 1, the electric field measurement device 901, however, is likely to be affected by a change in temperature around the electric field measurement device 901. Therefore, the electric field measurement device 901 may not measure an electric field with high sensitivity.

(Problems of Electric Field Detection Techniques of Patent Document 3)

Figure 17:
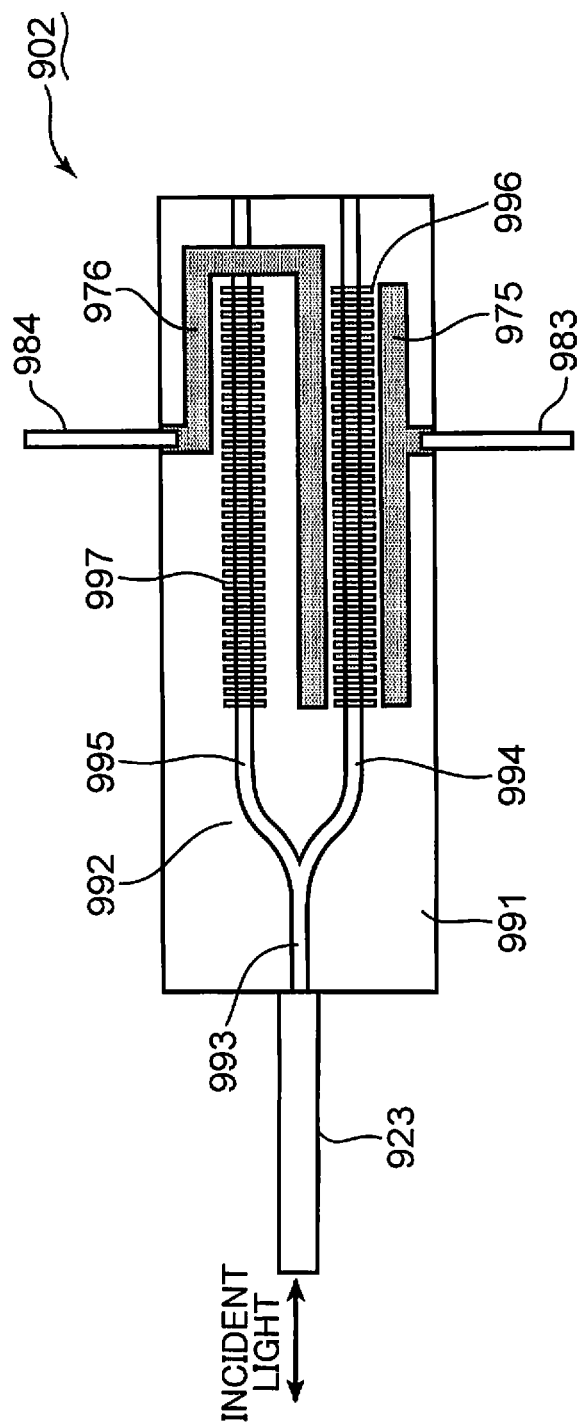
FIG. 17 is a schematic view of an electric field measurement device in Patent Document 3.

FIG. 17 is a schematic view of the electric field measurement device 902 of Patent Document 3. Problems of the electric field measurement device 902 of Patent Document 3 are described with reference to FIG. 17.

The electric field measurement device 902 includes an optical fiber 923, a substrate 991, electrodes 975, 976 and antennas 983, 984. The electric field measurement device 902 further includes an optical waveguide 992 formed on the substrate 991. The optical waveguide 992 includes a main waveguide 993 and branched waveguides 994, 995. The main waveguide 993 is connected to the optical fiber 923. The branched waveguide 994 branches from the main waveguide 993 and extends between the electrodes 975, 976. Like the branched waveguide 994, the branched waveguide 995 branches from the main waveguide 993. The branched waveguides 994, 995 are diffusion-type optical waveguides. The electric field measurement device 902 further includes a first grating 996 and a second grating 997. The first grating 996 is formed along the branched waveguide 994. The second grating 997 is formed along the branched waveguide 995. The first grating 996 is used for wavelength modulation. The second grating 997 is used for temperature compensation.

Incident light having a broadband spectrum enters the main waveguide 993 through the optical fiber 923. The incident light is divided into light propagating along the branched waveguide 994 and light propagating along the branched waveguide 995. The light propagating along the branched waveguide 994 enters the first grating 996. The light propagating along the branched waveguide 995 enters the second grating 997. Each of the first and second gratings 996, 997 causes Bragg diffraction of the incident light. Light components having a wavelength which satisfies a condition for Bragg diffraction is reflected by the first and second gratings 996, 997.

An electric field of a measurement target is applied to the first grating 996 through the antennas 983, 984 and the electrodes 975, 976. Consequently, there is a change in refractive index of the first grating 996. Therefore, a wavelength of reflected light returning toward the main waveguide 993 along the branched waveguide 994 changes in response to an application of the electric field.

The electric field measurement device 902 uses the wavelength of the reflected light from the second grating 997 as a reference to detect a difference between a wavelength of reflected light from the first grating 996 and a wavelength of reflected light from the second grating 997. Consequently, the electric field measurement device 902 may measure an electric field.

The electric field measurement device 902 needs a spectroscopic device for detecting a wavelength difference of reflected light. Therefore, the electric field measurement device 902 is disadvantageous in responsiveness of electric field detection. In addition, the electric field measurement device 902 becomes a large and expensive device.

First Embodiment

As described above, the conventional electric field measurement devices have various problems in terms of detection accuracy, size reduction and cost reduction. An electric field measurement device which contributes to solving the problems is described in the first embodiment.

FIG. 1 is a schematic view of the electric field measurement device 100 according to the first embodiment. The electric field measurement device 100 is described with reference to FIG. 1.

The electric field measurement device 100 includes an optical waveguide 200, an electrode portion 300, an antenna 400, a detector 500 and an applicator 600. Detection light DL used for detection of an electric field enters the optical waveguide 200. The detection light DL is transmitted by the optical waveguide 200. The detection light DL is then emitted from the optical waveguide 200. The detection light DL may be laser light. Alternatively, the detection light DL may be other light having a single wavelength. The principles of this embodiment are not limited to a specific type of the detection light DL. The optical waveguide 200 may be a step-type optical waveguide in which a one-dimensional rib, ridge structure or dielectric strip is mounted on a surface of a substrate (not shown). Alternatively, the optical waveguide 200 may have other structures configured to guide light. The principles of this embodiment are not limited to a specific structure of the optical waveguide 200. In this embodiment, the transmission light is exemplified by the detection light DL which is transmitted by the optical waveguide 200. The emission light is exemplified by the detection light DL which is emitted from the optical waveguide 200.

The detection light DL emitted from the optical waveguide 200 enters the detector 500. The detector 500 detects light intensity of the detection light DL.

The electrode portion 300 is formed along the transmission path of the detection light DL so as to give optical characteristics of the optical waveguide 200 a periodic variation. The electrode portion 300 may be formed in a comb shape. Alternatively, the electrode portion 300 may have an opening pattern which is repeated along the transmission path of the detection light DL. Further alternatively, the electrode portion 300 may have other shapes which give optical characteristics of the optical waveguide 200 a periodic variation in the propagating direction of the detection light DL. The principles of this embodiment are not limited in any way to a specific shape of the electrode portion 300.

The antenna 400 sets a first state, in which an electric field of a measurement target is coupled to the optical waveguide 200, and a second state, in which the electric field of the measurement target is disconnected from the optical waveguide 200. A user using the electric field measurement device 100 may get the antenna 400 closer to the measurement target to set the first state. The user may move the antenna 400 away from the measurement target to set the second state. Alternatively, a user may change an electrical connection between the antenna 400 and the applicator 600 to switch the coupling state of the electric field between the first and second states. The principles of this embodiment are not limited to a specific technique for switching the coupling state of the electric field. The antenna 400 may include a metal plate. Alternatively, the antenna 400 may have a rod antenna, folded antenna or other structures configured to be coupled electromagnetically to an electric field of a measurement target appropriately. The principles of this embodiment are not limited to a specific structure of the antenna 400.

The applicator 600 applies a voltage to the electrode portion 300. Consequently, the optical characteristics of the optical waveguide 200 vary periodically along the transmission direction of the detection light DL due to the shape of the electrode portion 300.

The detector 500 generates a first signal FS representing intensity of the detection light DL, which is detected under the first state, and a second signal SS representing intensity of the detection light DL, which is detected under the second state. The first signal FS is output from the electric field measurement device 100 as a detection signal representing an electric field of an measurement target. The second signal SS is output from the detector 500 to the applicator 600.

The applicator 600 includes a setting portion 610 and an output portion 620. When a user operates the antenna 400 to set the second state, the second signal SS is output from the detector 500 to the setting portion 610. The setting portion 610 sets a reference voltage in response to the second signal SS.

The output portion 620 applies a voltage to the electrode portion 300. When a user operates the antenna 400 to set the second state, the setting portion 610 changes a magnitude of the voltage applied to the electrode portion 300 through the output portion 620. Meanwhile, the setting portion 610 may find a voltage value, at which reflectivity of the optical waveguide 200 is maximized, from the second signal SS changing in response to the magnitude of the voltage. The setting portion 610 may set the voltage value, at which the reflectivity is maximized, as the reference voltage. The phrase "voltage value at which the reflectivity is maximized" may refer not only to a voltage value which results in the maximum value of the reflectivity but also to a voltage value close to the voltage value which results in the maximum value of the reflectivity.

Alternatively, the setting portion 610 may find a voltage value, at which a change in reflectivity of the optical waveguide 200 is maximized, from the second signal SS changing in response to a change in the magnitude of the voltage. The setting portion 610 may set the voltage value, at which the change in the reflectivity is maximized, as the reference voltage. The phrase "voltage value at which a change in reflectivity is maximized" may refer not only to a voltage value which results in a maximum value of a change in the reflectivity but also to a voltage value close to the voltage value which results in the maximum value of the change in the reflectivity.

Further alternatively, the setting portion 610 may find a voltage value, at which a difference between reflectivity and transmissivity of the optical waveguide 200 is minimized, from the second signal SS changing in response to a change in the magnitude of the voltage. The setting portion 610 may set the voltage value, at which the difference between the reflectivity and the transmissivity of the optical waveguide 200 is minimized, as a reference voltage. The phrase "voltage value, at which the difference between reflectivity and transmissivity is minimized" may refer not only to a voltage value which results in a minimum value of the difference between reflectivity and transmissivity but also to a voltage value close to the voltage value which results in the minimum value of the difference between reflectivity and transmissivity.

As described above, the setting portion 610 may use various setting methods to set a reference voltage. Therefore, the principles of this embodiment are not limited to a specific technique for setting a reference voltage.

When a user operates the antenna 400 to set the first state, an electric field of a measurement target is applied to the optical waveguide 200 and the electrode portion 300. Consequently, an induced voltage happens to the electrode portion 300. Meanwhile, the setting portion 610 outputs the reference voltage to the output portion 620. The output portion 620 connected to the antenna 400 applies a difference voltage to the electrode portion 300, a difference voltage corresponding to a difference between the reference voltage and the induced voltage caused by the application of the electric field of the measurement target.

While the output portion 620 applies the difference voltage, the electric field of the measurement target is measured accurately by the first signal FS output from the detector 500. Since the reference voltage is used, the electric field measurement device 100 is less likely to be affected by environmental variable factors such as a temperature change.

Second Embodiment

A designer may design various electric field measurement devices on the basis of the design principles described in the context of the first embodiment. An exemplary electric field measurement device is described in the second embodiment.

Figure 2:
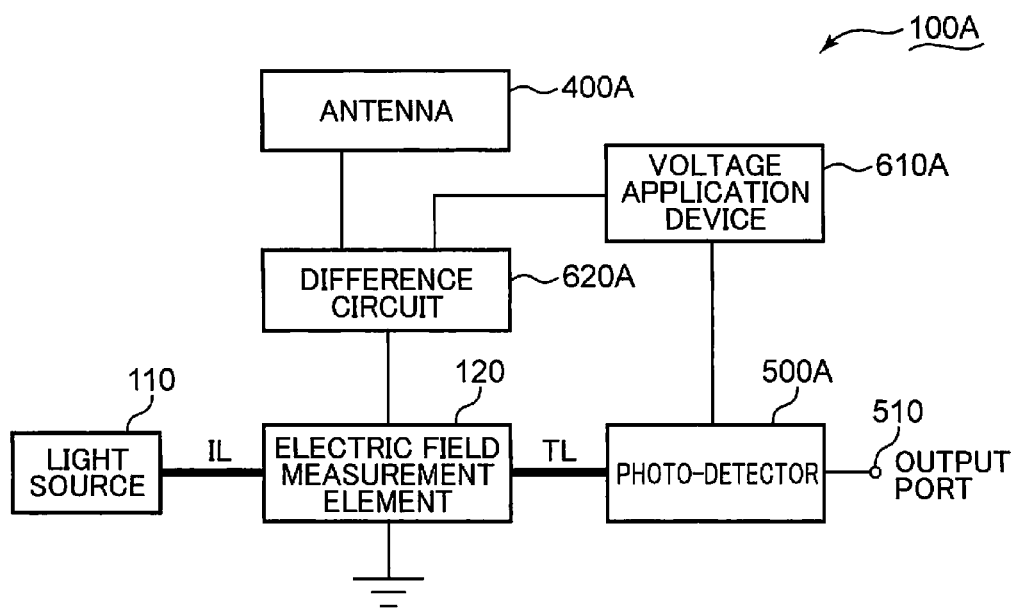
FIG. 2 is a schematic block diagram of an electric field measurement device according to the second embodiment.

FIG. 2 is a schematic block diagram of the electric field measurement device 100A according to the second embodiment. The electric field measurement device 100A is described with reference to FIGS. 1 and 2.

The electric field measurement device 100A includes a light source 110, an electric field measurement element 120, an antenna 400A, a photo-detector 500A, an output port 510, a voltage application device 610A and a difference circuit 620A. The light source 110 generates incident light IL, which enters the electric field measurement element 120. If the incident light IL is laser light, a laser source may be used as the light source 110. If the incident light IL is light having a single wavelength, a light-emitting diode may be used as the light source 110. The principles of this embodiment are not limited to a specific type of the light source 110. In this embodiment, the light source portion is exemplified by the light source 110.

The incident light IL becomes transmission light which is transmitted by the electric field measurement element 120. The transmission light is then emitted toward the photo-detector 500A as transmissive light TL which has passed through the electric field measurement element 120. The photo-detector 500A generates detection signals representing intensity of the transmissive light TL. The detection signals are output from the electric field measurement device 100A through the output port 510. In addition, the detection signals are output to the voltage application device 610A. The photo-detector 500A and the output port 510 correspond to the detector 500 described with reference to FIG. 1.

The voltage application device 610A connected to the photo-detector 500A is used for setting and outputting a reference voltage. The voltage application device 610A corresponds to the setting portion 610 described with reference to FIG. 1. The difference circuit 620A is connected to the voltage application device 610A and the antenna 400A.

The antenna 400A is used for selectively setting the first and second states. When the antenna 400A sets the first state, the difference circuit 620A applies a difference voltage to the electric field measurement element 120, the difference voltage corresponding to a difference between the reference voltage output from the voltage application device 610A and an induced voltage caused by the antenna 400A. The antenna 400A corresponds to the antenna 400 described with reference to FIG. 1. The difference circuit 620A corresponds to the output portion 620 described with reference to FIG. 1.

Figure 3:
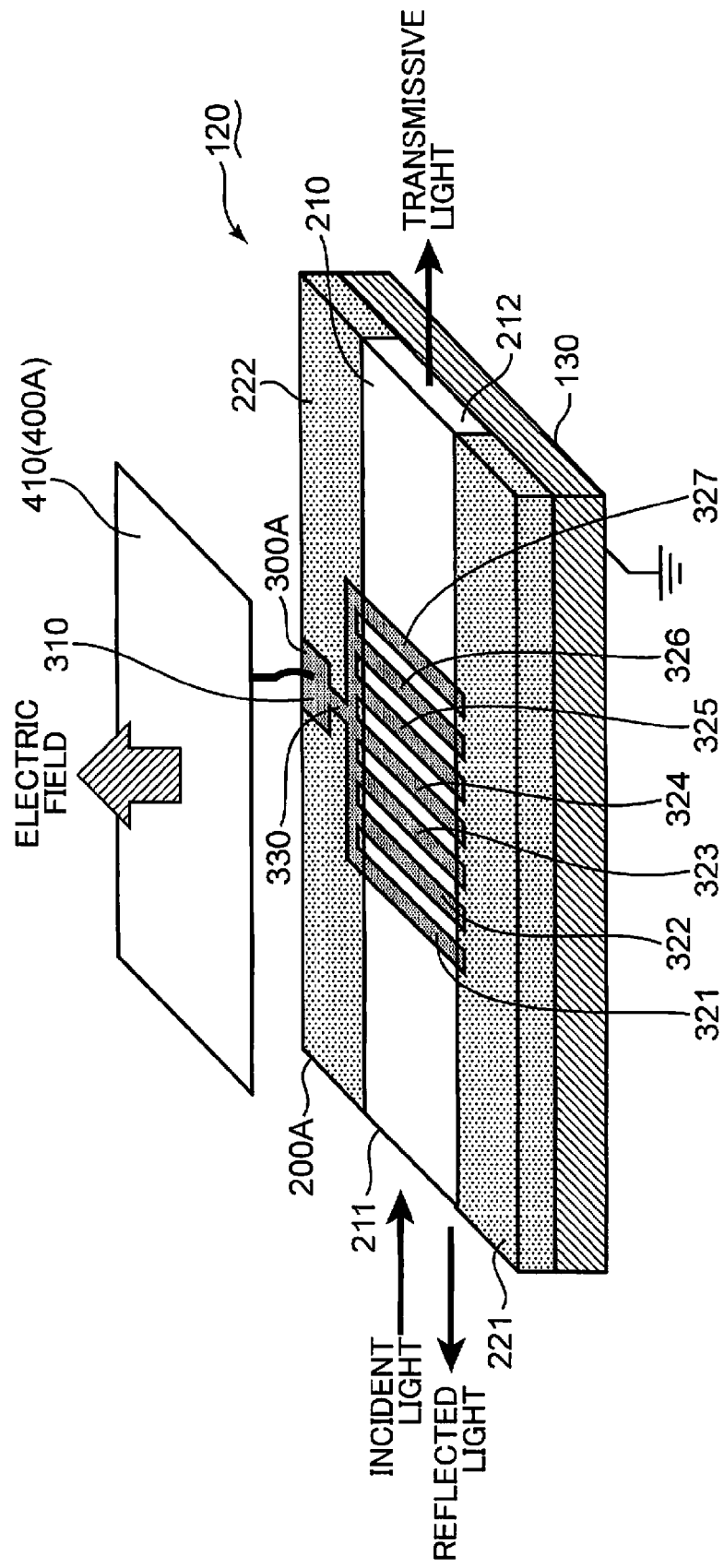
FIG. 3 is a schematic perspective view of an electric field measurement element of the electric field measurement device shown in FIG. 2.

FIG. 3 is a schematic perspective view of the electric field measurement element 120. The electric field measurement element 120 is described with reference to FIGS. 1 to 3.

The electric field measurement element 120 includes a substrate 130, an optical waveguide 200A and a pattern electrode 300A. The optical waveguide 200A is formed on the substrate 130. The pattern electrode 300A is formed on the optical waveguide 200A.

The optical waveguide 200A includes a core layer 210 and cladding layers 221, 222. The core layer 210 is an electro-optic crystal having six flat surfaces. The core layer 210 extends in the propagating direction of the incident light IL between the cladding layers 221, 222. The core layer 210 includes a first end surface 211 and a second end surface 212 opposite to the first end surface 211. The incident light IL enters the first end surface 211. The transmissive light TL is emitted from the second end surface 212. A part of the light guided by the core layer 210 is emitted from the first end surface 211 as reflected light. The optical waveguide 200A corresponds to the optical waveguide 200 described with reference to FIG. 1.

The pattern electrode 300A between the optical waveguide 200A and the antenna 400A is formed in a comb shape. The pattern electrode 300A includes a rectangular connection region 310, strip regions 321 to 327 and a substantially T-shaped intermediate region 330. The antenna 400A includes a metal plate 410. The metal plate 410 is connected to the connection region 310. In addition, the difference circuit 620A described with reference to FIG. 2 is also connected to the connection region 310. Each of the strip regions 321 to 327 extends across the core layer 210 in a direction intersecting with (substantially orthogonal to) the propagating direction of the light. The strip regions 321 to 327 are aligned to be distant from each other at substantially regular intervals in the propagating direction of the light. The pattern electrode 300A corresponds to the electrode portion 300 described with reference to FIG. 1. In this embodiment, the first electrode is exemplified by one of the strip regions 321 to 327. The second electrode is exemplified by another of the strip regions 321 to 327. The third electrode is exemplified by yet another of the strip regions 321 to 327.

In this embodiment, the pattern electrode 300A includes the seven strip regions 321 to 327. Alternatively, a pattern electrode may have two or more and less than seven strip regions. Further alternatively, a pattern electrode may have more than seven strip regions. A designer designing a pattern electrode may determine how many strip regions are provided so as to satisfy measurement accuracy required for an electric field measurement device. According to the present inventors, an electric field measurement device may measure an electric field of a measurement target with sufficiently high accuracy if a pattern electrode has five or more strip regions. The principles of this embodiment are not limited to a specific number of strip regions.

The substrate 130 is connected to the ground. Therefore, the substrate 130 may function as a ground electrode for the pattern electrode 300A. A metal larger than the substrate 130 may be used as the ground. Consequently, an electric field is coupled appropriately from the pattern electrode 300A to the optical waveguide 200A. Connection between the substrate 130 and the ground is not compulsory. The principles of this embodiment are not limited in any way by whether or not the substrate 130 is connected to the ground.

When an electric field of a measurement target is applied to the metal plate 410, an induced voltage happens to the pattern electrode 300A. Consequently, an electric field substantially orthogonal to the surface of the optical waveguide 200A, on which the pattern electrode 300A is formed, happens between the pattern electrode 300A and the substrate 130.

Figure 4:
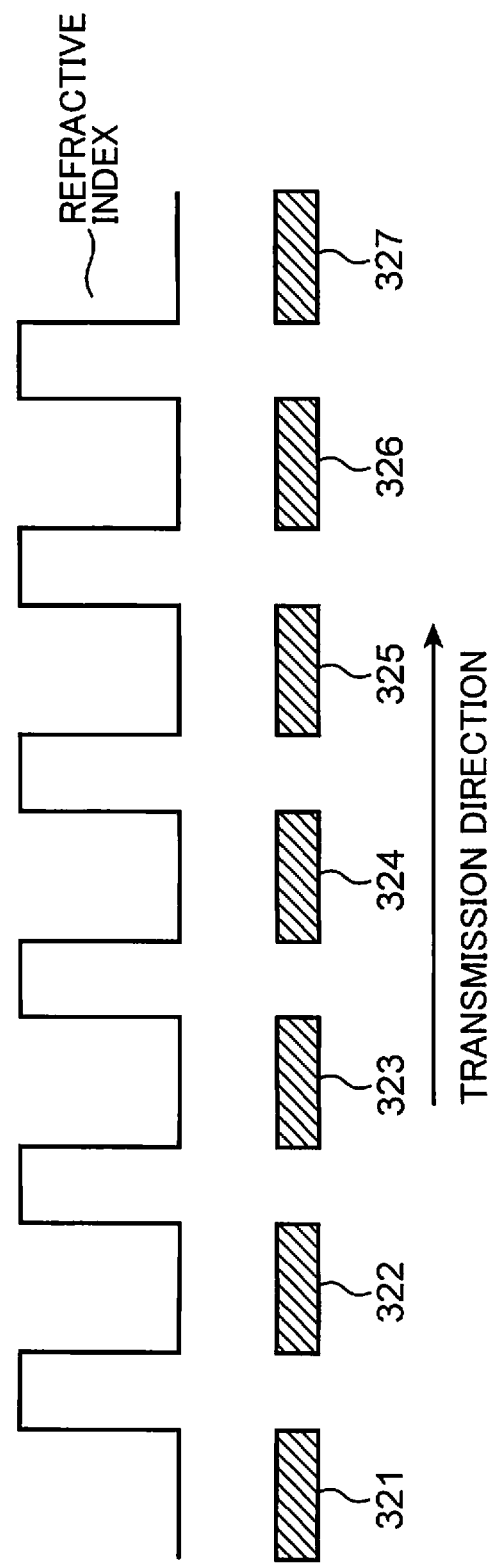
FIG. 4 is a schematic view of a refractive index distribution which occurs in a core layer of the electric field measurement element shown in FIG. 3.

FIG. 4 is a schematic view of a refractive index distribution which occurs in the core layer 210 under application of an electric field. The refractive index distribution under application of an electric field is described with reference to FIGS. 3 and 4.

When an electric field of a measurement target is coupled to the core layer 210 through the antenna 400A, a periodic refractive index distribution in correspondence to the shape (arrangement pattern of the strip regions 321 to 327) of the pattern electrode 300A occurs in the core layer 210. The refractive index of the core layer 210 is low at a position at which the strip regions 321 to 327 are formed. The refractive index of the core layer 210 is high at a position at which the strip regions 321 to 327 are absent. The variation width of the refractive index depends on a magnitude of the electric field of the measurement target.

Intensity of transmissive light and intensity of reflected light depend on the variation width of the refractive index. Therefore, if the intensity of transmissive light and/or reflected light is measured, an electric field of a measurement target is measured appropriately. The refractive index distribution of the core layer 210 is obtained by the pattern electrode 300A. Therefore, the principles of this embodiment do not need complex processes or high process accuracy for an electro-optic crystal utilized as the core layer 210.

The optical waveguide 200A may be formed by the epitaxial techniques. In this case, the substrate 130 is formed from a material suitable for forming the optical waveguide 200 as an epitaxial thin film. Therefore, a material utilized as the substrate 130 may have a crystal structure similar to the electro-optic crystal used as the optical waveguide 200A. In addition, the material of the substrate 130 may be selected so that a difference between the lattice constant of a material utilized as the substrate 130 and the lattice constant of an electro-optic crystal used as the optical waveguide 200A becomes 10% or less. Under the aforementioned condition, the optical waveguide 200A is formed efficiently by the epitaxial techniques. The principles of this embodiment are not limited to a specific relationship between a material of the optical waveguide 200A and a material of the substrate 130.

The substrate 130 functions as a ground electrode. Therefore, the material of the substrate 130 may be conductive. The following material may be suitably utilized for the substrate 130.

$SrTiO_3$ doped with Nb or alike

Oxide such as Al-doped ZnO, $In_2O_3$, $RuO_2$, $BaPbO_2$, $SrRuO_2$, $Mg_2TiO_4$ or $MgTi_2O_4$ Element semiconductor such as Si, Ge or diamond III-V compound semiconductor such as GaAs, GaSb, InP, InSb, or AlGaAs II-VI compound semiconductor such as ZnS, ZnSe, ZnTe or CaSe Metal such as Pt, Pd, Al or Ag Electro-optic crystal having an electro-optic effect such as lithium niobate ($LiNbO_3$), lithium tantalate ($LiTaO_3$), KTN ($KTa_{1-x}Nb_xO_3$ where x is ranged in $0<x<1$) or KTP ($KTiOPO_4$)

Light propagates in the core layer 210. Therefore, the substrate 130 may be formed from a material which has a lower refractive index than the core layer 210 does.

If the core layer 210 is formed from an oxide, the substrate 130 may be formed from the same oxide as the oxide of the core layer 210. In this case, Nb-doped SrTiO$_3$ is exemplified as a material of the substrate 130.

The pattern electrode 300A may be formed from various metals (e.g. Al, Ti, Cr, Ni, Cu, Pd, Ag, Ta, W, Pt or Au) or an alloy thereof. The pattern electrode 300A may be formed from transparent oxide (e.g. indium tin oxide (ITO) or Al-doped ZnO) which has a lower refractive index than the core layer 210 does. A material of the pattern electrode 300A may or may not satisfy an epitaxial relationship with a material of the optical waveguide 200A.

If the pattern electrode 300A is formed from a metal material and if frequency of light in the optical waveguide 200A exceeds the plasma frequency of the metal material, a part of light propagating in the optical waveguide 200A may leak at the pattern electrode 300A. Since the leaked light component is absorbed intensively by a carrier in the metal material, there is large propagation loss of light. Therefore, in terms of the light propagation loss, transparent oxide (e.g. indium tin oxide (ITO) or Al-doped ZnO) may be used as a material of the pattern electrode 300A.

The periodic distribution of refractive index shown in FIG. 4 serves as Bragg reflector. Therefore, a part of light propagating in the optical waveguide 200A is emitted from the first end surface 211 of the optical waveguide 200A as the reflected light. The wavelength of the light reflected by the periodic distribution of refractive index is determined by Bragg wavelength. If there is constant periodic variation amplitude of the refractive index under application of an electric field, Bragg wavelength depends on a period called grating period (i.e. structural period of the pattern electrode 300A). Therefore, a designer may determine a period of the pattern electrode 300A (i.e. interval of the strip regions 321 to 327) so that a wavelength of light propagating along the optical waveguide 200A becomes substantially as long as Bragg wavelength.

After a thin film electrode is formed on the optical waveguide 200A, a manufacturer may perform patterning processes on the thin film electrode to prepare the pattern electrode 300A.

The core layer 210 is formed from an electro-optic crystal having the electro-optic effect. Electro-optic crystals which may be used for forming the core layer 210 are exemplified by various electro-optic crystals such as LiNbO$_3$, LiTaO$_3$, KTN (KTa$_1$-xNbxO$_3$ where x is ranged in 0<x<1), and KTP. KTN has a large electro-optic coefficient among these electro-optic crystals. Therefore, KTN may be used as a material of the core layer 210.

KTN changes a crystal system from the cubic crystal system to the tetragonal crystal system in response to a surrounding temperature. KTN changes the crystal system from the cubic crystal system to the rhombohedral crystal system in other temperatures. If KTN is the cubic crystal system, KTN has the large secondary electro-optic effect.

In a temperature range close to a temperature of phase transition from the cubic crystal system to the tetragonal crystal system, KTN causes phenomena of divergence of relative permittivity. Since the secondary electro-optic effect is proportional to the power of the relative permittivity, there is a very large secondary electro-optic effect in KTN. The aforementioned characteristics of KTN allow the refractive index distribution shown in FIG. 4 to appear under a lower application voltage in comparison with other crystal materials. Therefore, if KTN is used for the core layer 210, the electric field measurement device 100A may detect an electric field of a measurement target with high sensitivity.

Light propagates along the core layer 210. Therefore, the cladding layers 221, 222 are formed from a material which has a lower refractive index than the core layer 210 does. The following materials may be suitably used for the cladding layers 221, 222.

Oxide such as SiO$_2$, TiO$_2$, ZrO$_2$, Nb$_2$O$_5$, Ta$_2$O$_5$, SnO$_2$, Al$_2$O$_3$ or MgO Element semiconductor such as Si, Ge or diamond III-V compound semiconductor such as GaAs, InP, InSb or AlGaAs Electro-optic crystal having an electro-optic effect such as LiNbO$_3$, LiTaO$_3$, KTN or KTP The electro-optic characteristics of various electro-optic crystals which are used for the aforementioned core layer 210 are likely to be susceptible to a change in temperature or humidity. Since the cladding layers 221, 222 surround the core layer 210 at least partially, a designer may select a material, which is less likely to be susceptible to a change in temperature or humidity, as the material of the cladding layers 221, 222, so that the core layer 210 is protected by the cladding layers 221, 222. For example, a designer may select SiO$_2$, which is less likely to be susceptible to a change in temperature or humidity, as the material of the cladding layers 221, 222.

Figure 5:
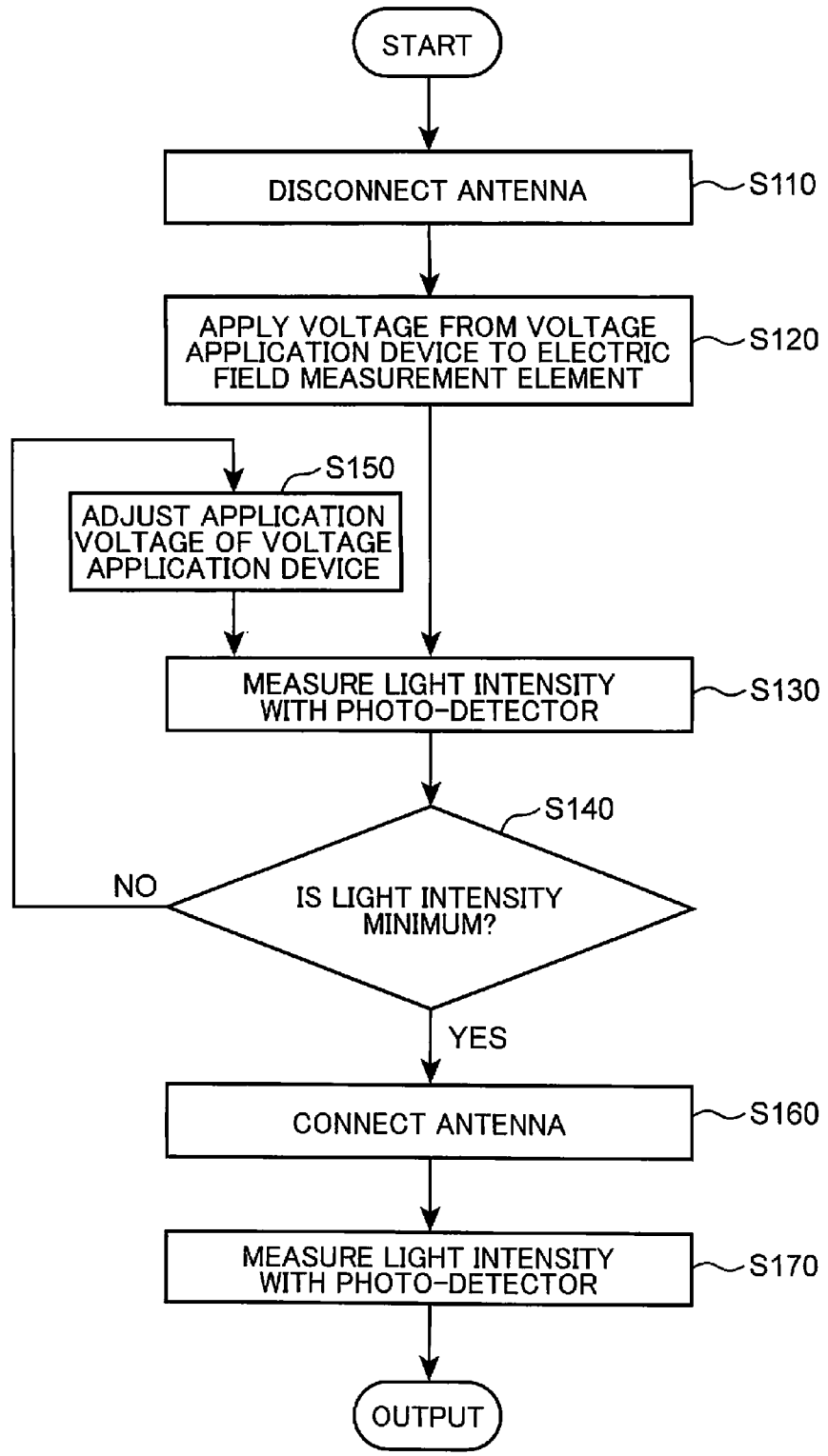
FIG. 5 is a schematic flowchart of an exemplary electric field measurement method which uses the electric field measurement device shown in FIG. 2.

FIG. 5 is a schematic flowchart of a method for measuring an exemplary electric field, in which the electric field measurement device 100A is used. The method for measuring an exemplary electric field is described with reference to FIGS. 2, 3 and 5.

(Step S110)

In step S110, a user using the electric field measurement device 100A sets the second state, in which an electric field of a measurement target is disconnected from the core layer 210. At this time, a terminal of the difference circuit 620A is connected to the ground. The user may disconnect the antenna 400A from the difference circuit 620A to set the second state. Alternatively, the user may move the antenna 400A sufficiently apart from the measurement target to set the second state. Step S120 is then executed.

(Step S120)

In step S120, the voltage application device 610A applies a voltage to the pattern electrode 300A through the difference circuit 620A. The light source 110 generates the incident light IL. The incident light IL propagates along the core layer 210. A periodic refractive index distribution occurs in the core layer 210 under the voltage application from the voltage application device 610A to the pattern electrode 300A. If the light propagating along the core layer 210 satisfies the conditions of Bragg diffraction, the light propagating along the core layer 210 is emitted from the first end surface 211 as the reflected light. Otherwise, the light propagating along the core layer 210 is emitted toward the photo-detector 500A from the second end surface 212 as the transmissive light TL. Step S130 is then executed.

(Step S130)

In step S130, the photo-detector 500A measures intensity of the transmissive light TL. The photo-detector 500A generates detection signals representing the intensity of the transmissive light TL. The detection signals are output from the photo-detector 500A to the voltage application device 610A. Step S140 is then executed.

(Step S140)

In step S140, the voltage application device 610A refers the detection signals to determine whether or not the intensity of the transmissive light TL is minimal. Unless the voltage application device 610A determines that the intensity of the transmissive light TL is minimal, step S150 is executed. Otherwise, step S160 is executed.

(Step S150)

In step S150, the voltage application device 610A changes a voltage value and then applies a voltage to the pattern electrode 300A. The processing loop from step S130 to step S150 is repeated until the voltage application device 610A determines that the intensity of the transmissive light TL becomes minimal.

(Step S160)

In step S160, the voltage application device 610A outputs a voltage to the difference circuit 620A as the reference voltage which causes the minimal intensity of the transmissive light TL. The user sets the first state in which the electric field of the measurement target is coupled to the core layer 210. The user may connect the antenna 400A to the difference circuit 620A to set the first state. Alternatively, the user may get the antenna 400A sufficiently closer to the measurement target to set the first state. Consequently, an induced voltage happens through the antenna 400A. The difference circuit 620A applies a difference voltage to the pattern electrode 300A, the difference voltage corresponding to a difference between the reference voltage and the induced voltage. Step S170 is then executed.

(Step S170)

In step S170, the photo-detector 500A generates detection signals representing intensity of the transmissive light TL under the first state. The detection signals are output from the electric field measurement device 100A through the output port 510.

Figure 6:
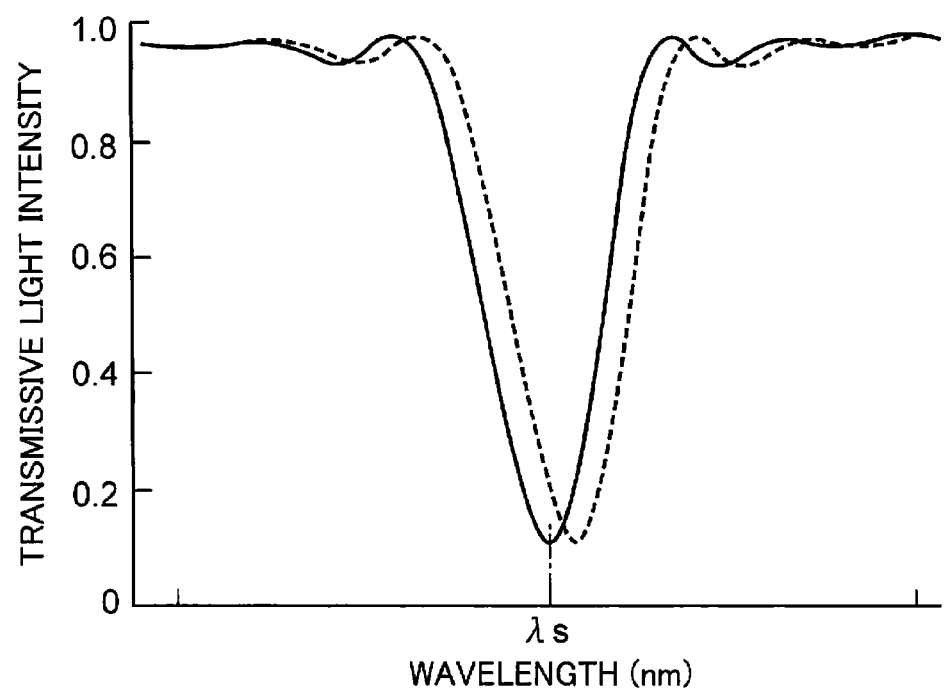
FIG. 6 is a schematic spectrum diagram of transmissive light.

FIG. 6 is a schematic spectrum diagram of the transmissive light TL. The method for measuring an electric field is further described with reference to FIGS. 2, 3, 5 and 6.

The symbol "λs" shown in FIG. 6 represents a wavelength of light propagating along the core layer 210. The solid line in FIG. 6 shows a spectrum diagram of the transmissive light TL under application of the reference voltage set by execution of the processing loop from step S130 to step S150 described with reference to FIG. 5. As shown in FIG. 6, the voltage application device 610A may make Bragg wavelength coincident to the wavelength of light propagating along the core layer 210 by execution of the processing loop from step S130 to step S150.

The dotted line shown in FIG. 6 shows a spectrum of the transmissive light TL when the electric field of the measurement target is applied to the core layer 210. As shown by the dotted line in FIG. 6, the Bragg wavelength changes in response to intensity of the electric field of the measurement target. Therefore, the intensity of the electric field of the measurement target is represented by a difference between the detection signals generated by the photo-detector 500A under the first and second states. An external device (not shown; e.g. personal computer) connected to the output port 510 may store data representing a relationship of intensity of the electric field with a difference between the detection signals generated by the photo-detector 500A under the first and second states in advance. The external device may calculate a difference between the detection signals generated by the photo-detector 500A under the first and second states, and compare the calculated difference value with the data stored in advance. Consequently, the electric field of the measurement target is measured accurately.

In the processing loop from step S130 to step S150, the electric field measurement element 120 functions as a reference element for obtaining a reference. In steps S160 and S170, the electric field measurement element 120 functions as a measurement element for measuring the electric field. Therefore, the electric field measurement device 100A is smaller and simpler than a conventional electric field measurement device which requires a reference element and a measurement element separate from the reference element.

The processing loop from step S130 to step S150 makes Bragg wavelength coincident to the wavelength of light propagating along the core layer 210 under various temperature conditions and various humidity conditions. Therefore, the electric field measurement device 100A may measure an electric field of a measurement target accurately under various environmental conditions.

A designer may design the electric field measurement device 100A without a spectroscopic element. Therefore, the electric field measurement device 100A may perform electric field measurement very responsively. In addition, the designer may give a small structure allowing easy fabrication to the electric field measurement device 100A.

Third Embodiment

The electric field measurement device according to the second embodiment measures an electric field of a measurement target from intensity of transmissive light. Alternatively, an electric field measurement device may measure an electric field of a measurement target from intensity of reflected light. An exemplary electric field measurement device which detects intensity of reflected light to measure an electric field of a measurement target is described in the third embodiment.

Figure 7:
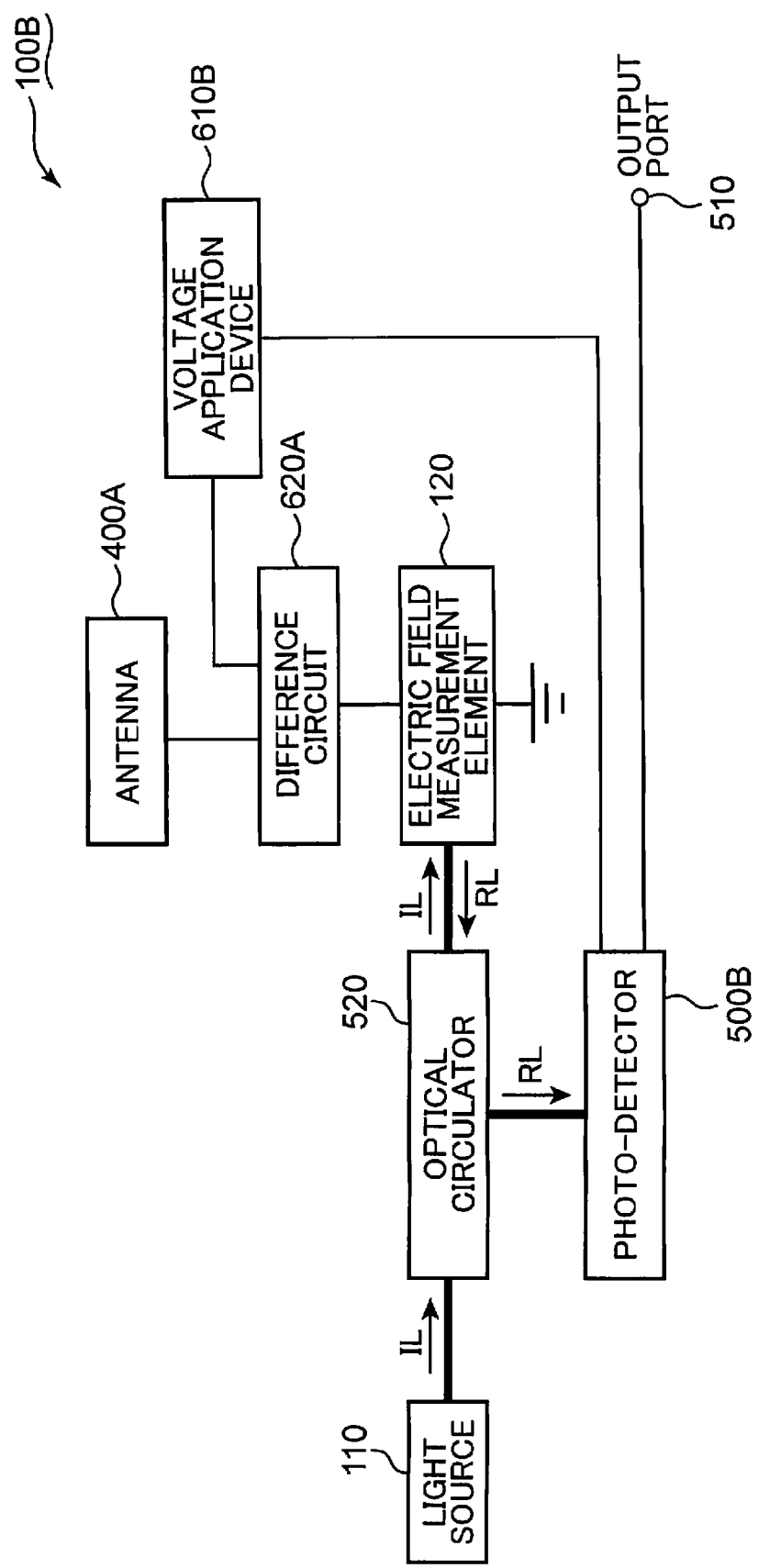
FIG. 7 is a schematic block diagram of an electric field measurement device according to the third embodiment.

FIG. 7 is a schematic block diagram of the electric field measurement device 100B according to the third embodiment. The electric field measurement device 100B is described with reference to FIGS. 1 to 7. Reference signs used commonly between the second and third embodiments indicate that components denoted by the common reference signs have the same functions as the second embodiment. Therefore, the description of the second embodiment is applicable to these components.

Like the second embodiment, the electric field measurement device 100B includes the light source 110, the electric field measurement element 120, the antenna 400A, the output port 510 and the difference circuit 620A. The description of the second embodiment is applicable to these components.

The electric field measurement device 100B further includes a photo-detector 500B, an optical circulator 520 and a voltage application device 610B. The photo-detector 500B is connected to the output port 510 and the voltage application device 610B. The optical circulator 520 is situated between the light source 110 and the electric field measurement element 120. The voltage application device 610B is connected to the difference circuit 620A. The photo-detector 500B, the output port 510 and the optical circulator 520 correspond to the detector 500 described with reference to FIG. 1. The voltage appliance device 610B corresponds to the setting portion 610 described with reference to FIG. 1.

Like the second embodiment, the light source 110 generates the incident light IL. The incident light IL enters the electric field measurement element 120 through the optical circulator 520.

Like the second embodiment, the voltage application device 610B applies a voltage to the electric field measurement element 120 through the difference circuit 620A under the second state and makes Bragg wavelength coincident to a wavelength of light propagating in the electric field measurement element 120. Consequently, intensive reflected light RL is emitted from the electric field measurement element 120. The reflected light RL is directed toward the photo-detector 500B by the optical circulator 520. Consequently, the reflected light RL enters the photo-detector 500B. The photo-detector 500B generates detection signals representing intensity of the reflected light RL. The detection signals are output from the electric field measurement device 100B through the output port 510.

A user then operates the antenna 400A to couple an electric field of a measurement target to the electric field measurement element 120 and set the first state. Consequently, there is a change in Bragg wavelength. Therefore, the intensity of the reflected light RL detected by the photo-detector 500B also changes. The photo-detector 500B generates detection signals representing the intensity of the reflected light RL. The detection signals are output from the electric field measurement device 100B through the output port 510.

Like the second embodiment, a difference between the detection signals output under the first and second states indicates the intensity of the electric field of the measurement target. Therefore, the electric field measurement device 100B may accurately measure the intensity of the electric field of the measurement target.

Figure 8:
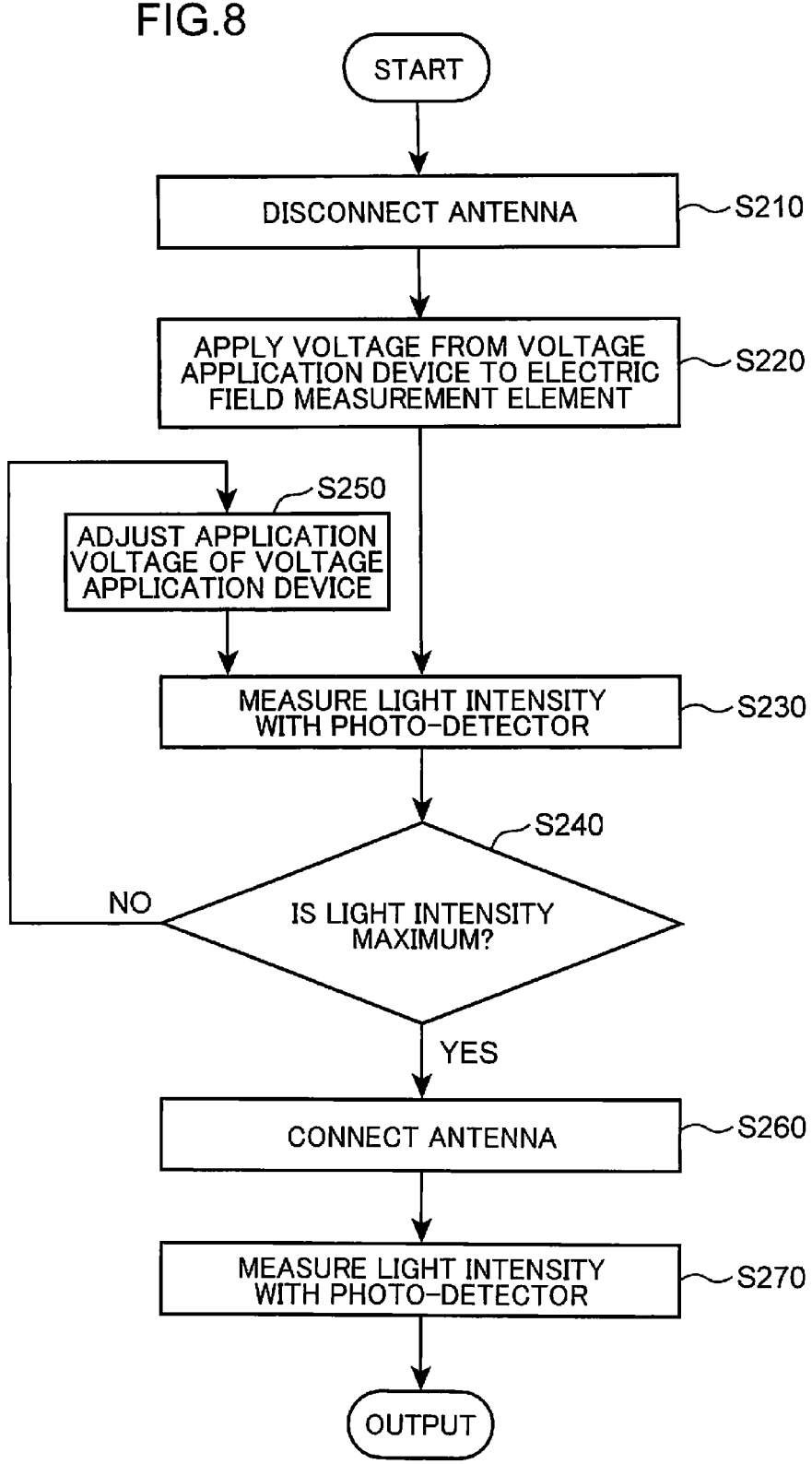
FIG. 8 is a schematic flowchart of an exemplary electric field measurement method which uses the electric field measurement device shown in FIG. 7.

FIG. 8 is a schematic flowchart of an exemplary method for measuring an electric field in which the electric field measurement device 100B is used. The exemplary method for measuring an electric field is described with reference to FIGS. 3, 6 to 8.

(Step S210)

In step S210, a user using the electric field measurement device 100B sets the second state in which an electric field of a measurement target is disconnected from the core layer 210. At this time, the terminal of the difference circuit 620A is connected to the ground. The user may disconnect the antenna 400A from the difference circuit 620A to set the second state. Alternatively, the user may move the antenna 400A sufficiently apart from the measurement target to set the second state. Step S220 is then executed.

(Step S220)

In step S220, the voltage application device 610B applies a voltage to the pattern electrode 300A through the difference circuit 620A. The light source 110 generates the incident light IL. The incident light IL propagates along the core layer 210. A periodic refractive index distribution occurs in the core layer 210 under the voltage application from the voltage application device 610B to the pattern electrode 300A. If light propagating along the core layer 210 satisfies the conditions for Bragg diffraction, the light propagating along the core layer 210 is emitted from the first end surface 211 as the reflected light RL. The reflected light RL is then emitted to the photo-detector 500B through the circulator 520. Otherwise, the light propagating along the core layer 210 is emitted from the second end surface 212 as the transmissive light. Step S230 is then executed.

(Step S230)

In step S230, the photo-detector 500B measures intensity of the reflected light RL. The photo-detector 500B generates detection signals representing the intensity of the reflected light RL. The detection signals are output to the voltage application device 610B from the photo-detector 500B. Step S240 is then executed.

(Step S240)

In step S240, the voltage application device 610B refers the detection signals to determine whether or not the intensity of the reflected light RL is maximal. Unless the voltage application device 610B determines that the intensity of the reflected light RL is maximal, step S250 is executed. Otherwise, step S260 is executed.

(Step S250)

In step S250, the voltage application device 610B changes a voltage value, and then applies a voltage to the pattern electrode 300A. The processing loop of step S230 to step S250 is repeated until the voltage application device 610B determines that the intensity of the reflected light RL is maximal.

(Step S260)

In step S260, the voltage application device 610B outputs a voltage to the difference circuit 620A as the reference voltage at which the intensity of the reflected light RL is maximized. The user sets the first state in which the electric field of the measurement target is coupled to the core layer 210. The user may connect the antenna 400A to the difference circuit 620A to set the first state. Alternatively, the user may get the antenna 400A sufficiently closer to the measurement target to set the first state. Consequently, an induced voltage occurs through the antenna 400A. The difference circuit 620A applies a difference voltage to the pattern electrode 300A, the difference voltage corresponding to a difference between the reference voltage and the induced voltage. Step S270 is then executed.

(Step S270)

In step S270, the photo-detector 500B generates detection signals representing intensity of the reflected light RL under the first state. The detection signals are output from the electric field measurement device 100B through the output port 510.

The intensity of the reflected light RL has an inverse relationship with the intensity of the transmissive light shown in FIG. 6. In short, when "λs" is the wavelength of light propagating along the core layer 210, the intensity of the reflected light RL is maximized under the second state.

The voltage application device 610B executes the processing loop of step S230 to S250 to make Bragg wavelength coincident to a wavelength of light propagating along the core layer 210. Consequently, the intensity of the reflected light RL is maximized when "λs" is the wavelength of light propagating along the core layer 210.

As described in the context of the second embodiment, Bragg wavelength changes in response to intensity of an electric field of a measurement target. Therefore, the intensity of the electric field of the measurement target is represented by a difference between the detection signals generated by the photo-detector 500B under the first and second states. An external device (not shown; e.g. personal computer) connected to the output port 510 may store data in advance, the data representing a relationship of the intensity of the electric field with the difference between the detection signals generated by the photo-detector 500B under the first and second states. The external device may calculate the difference between the detection signals generated by the photo-detector 500B under the first and second states, and then compare the calculated difference value with the data which is stored in advance. Consequently, the electric field of the measurement target is measured accurately.

In the processing loop from step S230 to step S250, the electric field measurement element 120 functions as a reference element for obtaining a reference. In steps S260 and S270, the electric field measurement element 120 functions as a measurement element for measuring an electric field. Therefore, the electric field measurement device 100B is smaller and simpler than a conventional electric field measurement device which requires a reference element and a measurement element separate from the reference element.

The processing loop from step S230 to step S250 makes Bragg wavelength coincident to a wavelength of light propagating along the core layer 210 under various temperature conditions and various humidity conditions. Therefore, the electric field measurement device 100B may measure an electric field of a measurement target accurately under various environmental conditions.

A designer may design the electric field measurement device 100B without a spectroscopic element. Therefore, the electric field measurement device 100B may perform electric field measurement with high responsiveness. In addition, the designer may give the electric field measurement device 100B a small structure which allows easy fabrication.

Fourth Embodiment

The electric field measurement device according to the second embodiment measures an electric field of a measurement target from intensity of transmissive light. The electric field measurement device according to the third embodiment measures an electric field of a measurement target from intensity of reflected light. Alternatively, an electric field measurement device may measure an electric field of a measurement target from intensity of transmissive light and reflected light. An exemplary electric field measurement device which detects intensity of transmissive light and reflected light to measure an electric field of a measurement target is described in the fourth embodiment.

Figure 9:
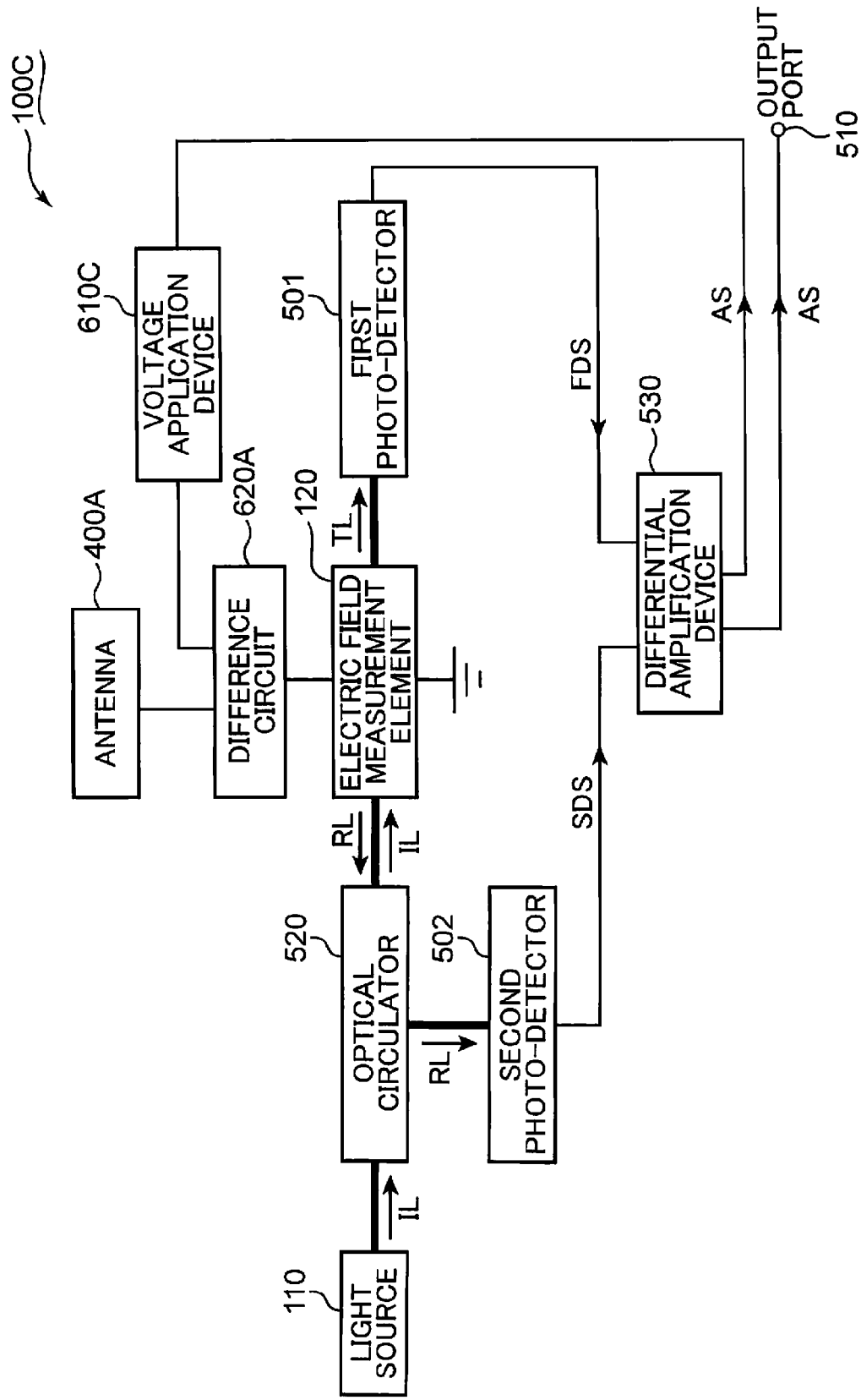
FIG. 9 is a schematic block diagram of an electric field measurement device according to the fourth embodiment.

FIG. 9 is a schematic block diagram of the electric field measurement device 1000 according to the fourth embodiment. The electric field measurement device 100C is described with reference to FIGS. 1 and 9. Reference signs used commonly between the second to fourth embodiments indicate that components denoted by the common reference signs have the same functions as the second or third embodiment. Therefore, the description of the second or third embodiment is applicable to these components.

Like the second embodiment, the electric field measurement device 100C includes the light source 110, the electric field measurement element 120, the antenna 400A, the output port 510 and the difference circuit 620A. The description of the second embodiment is applicable to these components.

Like the third embodiment, the electric field measurement device 100C further includes the optical circulator 520. The description of the third embodiment is applicable to the optical circulator 520.

The electric field measurement device 100C further includes a first photo-detector 501, a second photo-detector 502, a differential amplification device 530 and a voltage application device 610C. The first and second photo-detectors 501, 502 are connected to the differential amplification device 530. The differential amplification device 530 is connected to the output port 510 and the voltage application device 610C. The first photo-detector 501, the second photo-detector 502, the output port 510, the optical circulator 520 and the differential amplification device 530 correspond to the detector 500 described with reference to FIG. 1. The voltage application device 610C corresponds to the setting portion 610 described with reference to FIG. 1.

The first photo-detector 501 receives the transmissive light TL passing through the electric field measurement element 120. The first photo-detector 501 generates a first detection signal FDS representing intensity of the transmissive light TL. The first detection signal FDS is output from the first photo-detector 501 to the differential amplification device 530. In this embodiment, the first electrical signal is exemplified by the first detection signal FDS. The first photo-detector is exemplified by the first photo-detector 501.

The optical circulator 520 directs the reflected light RL toward the second photo-detector 502, the reflected light RL being emitted from the electric field measurement element 120. Accordingly, the second photo-detector 502 receives the reflected light RL. The second photo-detector 502 generates a second detection signal SDS representing intensity of the reflected light RL. The second detection signal SDS is output from the second photo-detector 502 to the differential amplification device 530. In this embodiment, the second electrical signal is exemplified by the second detection signal SDS. The second photo-detector is exemplified by the second photo-detector 502.

The differential amplification device 530 performs difference arithmetic processes for the first and second detection signals FDS, SDS. The differential amplification device 530 amplifies a difference between the first and second detection signals FDS, SDS. In this embodiment, the amplifier is exemplified by the differential amplification device 530.

Figure 10:
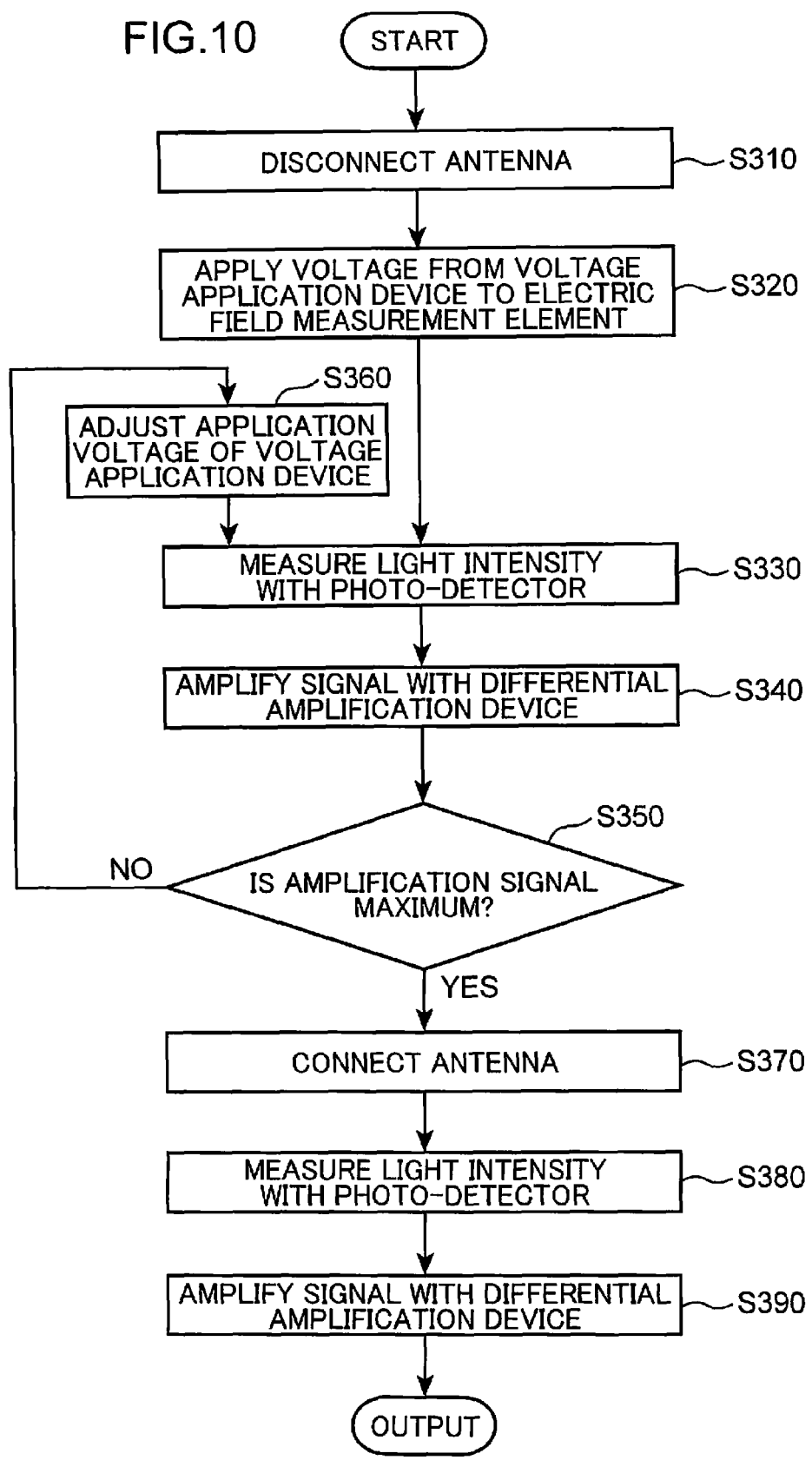
FIG. 10 is a schematic flowchart of an exemplary electric field measurement method which uses the electric field measurement device shown in FIG. 9.

FIG. 10 is a schematic flowchart of an exemplary method for measuring an electric field in which the electric field measurement device 100C is used. The exemplary method for measuring an electric field is described with reference to FIGS. 3, 6, 9 and 10.

(Step S310)

In step S310, a user using the electric field measurement device 100C sets the second state, in which an electric field of a measurement target is disconnected from the core layer 210. At this time, the terminal of the difference circuit 620A is connected to the ground. The user may disconnect the antenna 400A from the difference circuit 620A to set the second state. Alternatively, the user may move the antenna 400A sufficiently apart from the measurement target to set the second state. Step S320 is then executed.

(Step S320)

In step S320, the voltage application device 610C applies a voltage to the pattern electrode 300A through the difference circuit 620A. The light source 110 generates the incident light IL. The incident light IL propagates along the core layer 210. A periodic refractive index distribution occurs in the core layer 210 under the voltage application from the voltage application device 610C to the pattern electrode 300A. If light propagating along the core layer 210 satisfies the conditions for Bragg diffraction, the light propagating along the core layer 210 is emitted from the first end surface 211 to the second photo-detector 502 through the optical circulator 520 as the reflected light RL. Otherwise, the light propagating along the core layer 210 is emitted from the second end surface 212 to the first photo-detector 501 as the transmissive light TL. Step S330 is then executed.

(Step S330)

In step S330, the first photo-detector 501 generates the first detection signal FDS representing intensity of the transmissive light TL. The first detection signal FDS is output from the first photo-detector 501 to the differential amplification device 530. The second photo-detector 502 generates a second detection signal SDS representing intensity of the reflected light RL. The second detection signal SDS is output from the second photo-detector 502 to the differential amplification device 530. Step S340 is then executed.

(Step S340)

In step S340, the differential amplification device 530 performs difference arithmetic processes for the first and second detection signals FDS, SDS. The differential amplification device 530 amplifies a difference between the first and second detection signals FDS, SDS to generate an amplification signal AS. The amplification signal AS is output from the differential amplification device 530 to the voltage application device 610C and the output port 510. Step S350 is then executed.

(Step S350)

In step S350, the voltage application device 610C refers the amplification signal AS to determine whether or not the amplification signal AS is maximized. Unless the voltage application device 610C determines that the amplification signal AS is maximal, step S360 is executed. Otherwise, step S370 is executed.

(Step S360)

In step S360, the voltage application device 610C changes a voltage value, and then applies a voltage to the pattern electrode 300A. The processing loop from step S330 to step S360 is repeated until the voltage application device 610C determines that the amplification signal AS is maximal.

(Step S370)

In step S370, the voltage application device 610C outputs a voltage to the difference circuit 620A as a reference voltage at which the amplification signal AS becomes maximal. The user sets the first state in which the electric field of the measurement target is coupled to the core layer 210. The user may connect the antenna 400A to the difference circuit 620A to set the first state. Alternatively, the user may get the antenna 400A sufficiently closer to the measurement target to set the first state. Consequently, an induced voltage occurs through the antenna 400A. The difference circuit 620A applies a difference voltage to the pattern electrode 300A, the difference voltage corresponding to a difference between the reference voltage and the induced voltage. Step S380 is then executed.

(Step S380)

In step S380, the first photo-detector 501 generates a first detection signal FDS representing intensity of the transmissive light TL under the first state. The first detection signal FDS is output from the first photo-detector 501 to the differential amplification device 530. The second photo-detector 502 generates a second detection signal SDS representing intensity of the reflected light RL under the first state. The second detection signal SDS is output from the second photo-detector 502 to the differential amplification device 530. Step S390 is then executed.

(Step S390)

In step S390, the differential amplification device 530 performs difference arithmetic processes for the first and second detection signals FDS, SDS. The differential amplification device 530 amplifies a difference between the first and second detection signals FDS, SDS to generate an amplification signal AS. The amplification signal AS is output from the differential amplification device 530 to the voltage application device 610C and the output port 510.

Bragg wavelength is coincident to the wavelength "λs" of light propagating along the core layer 210 when the amplification signal AS is maximized. In short, intensity of the transmissive light TL detected by the first photo-detector 501 is minimized whereas intensity of the reflected light RL detected by the second photo-detector 502 is maximized.

The voltage application device 610C executes the processing loop from step S330 to S360 to make Bragg wavelength coincident to a wavelength of light propagating along the core layer 210. Consequently, the amplification signal AS is maximized when "λs" is the wavelength of the light propagating along the core layer 210.

As described in the context of the second embodiment, Bragg wavelength changes in response to intensity of an electric field of a measurement target. Therefore, the intensity of the electric field of the measurement target is represented by a difference between the amplification signals AS generated by the differential amplification device 530 under the first and second states. An external device (not shown; e.g. personal computer) connected to the output port 510 may store data in advance, the data representing a relationship of the intensity of the electric field with the difference between the amplification signals AS generated by the differential amplification device 530 under the first and second states. The external device may calculate the difference of the amplification signals AS generated by the differential amplification device 530 under the first and second states, and then compare the calculated difference value with the data which is stored in advance. Consequently, the electric field of the measurement target is measured accurately.

Since the electric field measurement device 100C uses the differential amplification device 530 to measure an electric field, the electric field measurement device 100C may use a signal having amplitude twice as large as that of the detection techniques described in the context of the second and third embodiments to measure the electric field. Therefore, noise of light emitted from the light source 110 is relatively reduced. Consequently, the electric field measurement device 100C may measure an electric field of a measurement target accurately.

In the processing loop from step S330 to step S360, the electric field measurement element 120 functions as a reference element for obtaining a reference. In steps S380 and S390, the electric field measurement element 120 functions as a measurement element for measuring an electric field. Thus, the electric field measurement device 100C is smaller and simpler than a conventional electric field measurement device which requires a reference element and a measurement element separate from the reference element.

The processing loop from step S330 to step S360 makes the Bragg wavelength coincident to a wavelength of light propagating along the core layer 210 under various temperature conditions and various humidity conditions. Therefore, the electric field measurement device 100C may measure an electric field of a measurement target accurately under various environmental conditions.

A designer may design the electric field measurement device 100C without a spectroscopic element. Therefore, the electric field measurement device 100C may perform electric field measurement very responsively. In addition, a designer may give the electric field measurement device 100C a small structure which allows easy fabrication.

Fifth Embodiment

In the fourth embodiment, the electric field measurement device sets a voltage as a reference voltage at which an amplification signal generated by the differential amplification device becomes maximal. Alternatively, an electric field measurement device may set a voltage as a reference voltage at which an amplification signal generated by a differential amplification device becomes minimal. An electric field measurement device configured to set a voltage as a reference voltage at which an amplification signal generated by a differential amplification device becomes minimal is described in the fifth embodiment.

Figure 11:
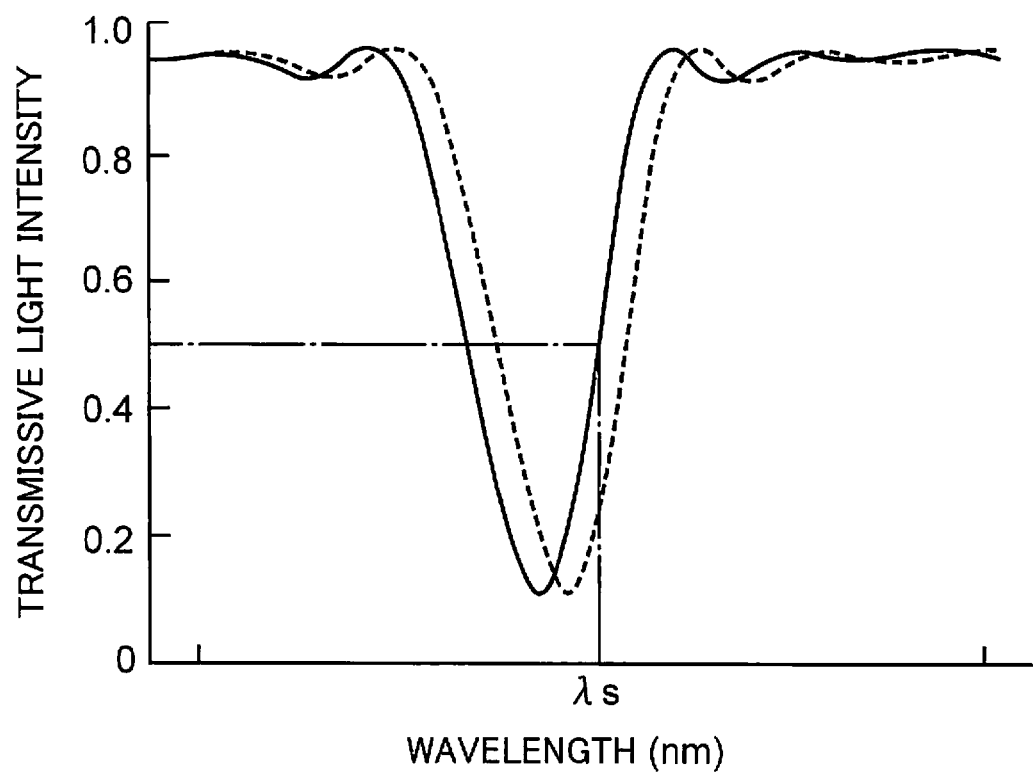
FIG. 11 is a schematic spectrum diagram of transmissive light emitted from an electric field measurement element of the electric field measurement device shown in FIG. 9 (the fifth embodiment).

FIG. 11 is a schematic spectrum diagram of the transmissive light TL emitted from the electric field measurement element 120 of the electric field measurement device 100C described with reference to FIG. 9. Operations of the electric field measurement device 100C are described with reference to FIGS. 3, 9 and 11.

The symbol "λs" shown in FIG. 11 represents a wavelength of light propagating along the core layer 210. The voltage application device 610C sets a voltage as the reference voltage if intensity of the transmissive light TL emitted from the electric field measurement element 120 becomes coincident to intensity of the reflected light RL emitted from the electric field measurement element 120 at the voltage. In short, the voltage application device 610C sets a voltage as the reference voltage if the amplification signal AS generated by the differential amplification device 530 is minimized at the voltage.

The voltage application device 610C applies the reference voltage to the pattern electrode 300A through the difference circuit 620A. When a user uses the antenna 400A to set the first state, an electric field is coupled to the core layer 210. Consequently, the intensity of each of the transmissive light TL and the reflected light RL which are emitted from the electric field measurement element 120 changes as represented by the dotted line in FIG. 11. The amplification signal AS output from the differential amplification device 530 also changes in response to the change in intensity of the transmissive light TL and the reflected light RL.

Figure 12:
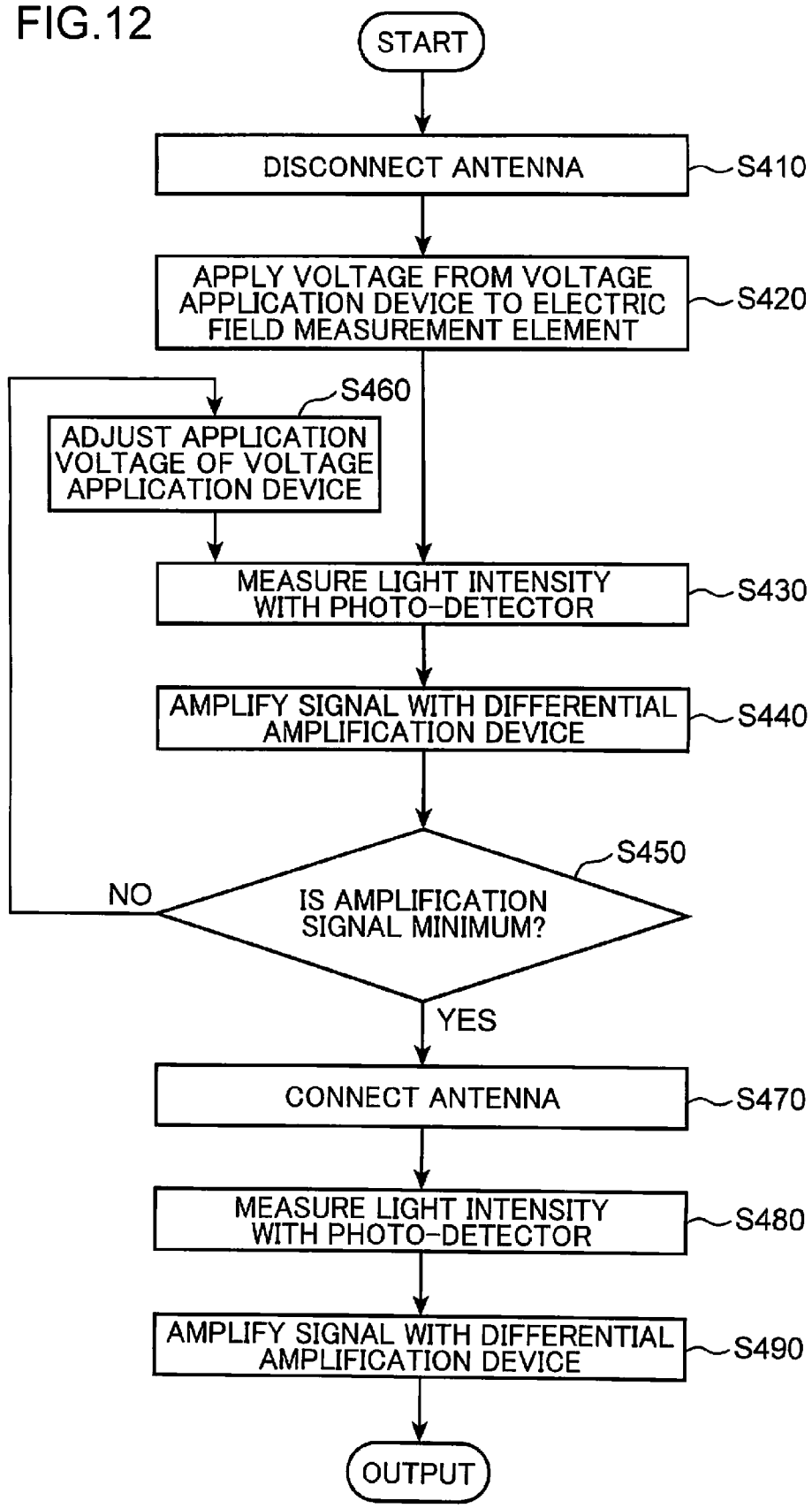
FIG. 12 is a schematic flowchart of an exemplary electric field measurement method which uses the electric field measurement device shown in FIG. 9 (the fifth embodiment).

FIG. 12 is a schematic flowchart of an exemplary method for measuring an electric field in which the electric field measurement device 100C is used. The exemplary method for measuring an electric field is described with reference to FIGS. 3, 11, 9 to 12.

(Step S410)

In step S410, a user using the electric field measurement device 100C sets the second state in which an electric field of a measurement target is disconnected from the core layer 210. At this time, the terminal of the difference circuit 620A is connected to the ground. The user may disconnect the antenna 400A from the difference circuit 620A to set the second state. Alternatively, the user may move the antenna 400A sufficiently apart from the measurement target to set the second state. Step S420 is then executed.

(Step S420)

In step S420, the voltage application device 610C applies a voltage to the pattern electrode 300A through the difference circuit 620A. The light source 110 generates the incident light IL. The incident light IL propagates along the core layer 210. A periodic refractive index distribution occurs in the core layer 210 under the voltage application from the voltage application device 610C to the pattern electrode 300A. If light propagating along the core layer 210 satisfies the conditions for Bragg diffraction, the light propagating along the core layer 210 is emitted as the reflected light RL from the first end surface 211 to the second photo-detector 502 through the optical circulator 520. Otherwise, the light propagating along the core layer 210 is emitted as the transmissive light TL from the second end surface 212 to the first photo-detector 501. Step S430 is then executed.

(Step S430)

In step S430, the first photo-detector 501 generates the first detection signal FDS representing intensity of the transmissive light TL. The first detection signal FDS is output from the first photo-detector 501 to the differential amplification device 530. The second photo-detector 502 generates the second detection signal SDS representing intensity of the reflected light RL. The second detection signal SDS is output from the second photo-detector 502 to the differential amplification device 530. Step S440 is then executed.

(Step S440)

In step S440, the differential amplification device 530 performs difference arithmetic processes for the first and second detection signals FDS, SDS. The differential amplification device 530 amplifies a difference between the first and second detection signals FDS, SDS to generate the amplification signal AS. The amplification signal AS is output from the differential amplification device 530 to the voltage application device 610C and the output port 510. Step S450 is then executed.

(Step S450)

In step S450, the voltage application device 610C refers the amplification signal AS to determine whether or not the amplification signal AS is minimal. Unless the voltage application device 610C determines that the amplification signal AS is minimal, step S460 is executed. Otherwise, step S470 is executed.

(Step S460)

In step S460, the voltage application device 610C changes a voltage value, and then applies a voltage to the pattern electrode 300A. The processing loop from step S430 to step S460 is repeated until the voltage application device 610C determines that the amplification signal AS is minimal.

(Step S470)

In step S470, the voltage application device 610C outputs a voltage to the difference circuit 620A as the reference voltage at which the amplification signal AS becomes minimal. The user sets the first state in which the electric field of the measurement target is coupled to the core layer 210. The user may connect the antenna 400A to the difference circuit 620A to set the first state. Alternatively, the user may get the antenna 400A sufficiently closer to the measurement target to set the first state. Consequently, an induced voltage occurs through the antenna 400A. The difference circuit 620A applies a difference voltage to the pattern electrode 300A, the difference voltage corresponding to the difference between the reference voltage and the induced voltage. Step S480 is then executed.

(Step S480)

In step S480, the first photo-detector 501 generates the first detection signal FDS representing intensity of the transmissive light TL under the first state. The first detection signal FDS is output from the first photo-detector 501 to the differential amplification device 530. The second photo-detector 502 generates the second detection signal SDS representing intensity of the reflected light RL under the first state. The second detection signal SDS is output from the second photo-detector 502 to the differential amplification device 530. Step S490 is then executed.

(Step S490)

In step S490, the differential amplification device 530 performs difference arithmetic processes for the first and second detection signals FDS, SDS. The differential amplification device 530 amplifies a difference between the first and second detection signals FDS to generate the amplification signal AS. The amplification signal AS is output from the differential amplification device 530 to the voltage application device 610C and the output port 510.

As described with reference to FIG. 11, Bragg wavelength changes in response to intensity of an electric field of a measurement target. Therefore, the intensity of the electric field of the measurement target is represented by a difference between the amplification signals AS generated by the differential amplification device 530 under the first and second states. An external device (not shown; e.g. personal computer) connected to the output port 510 may store data in advance, the data representing a relationship of the intensity of the electric field with a difference between the amplification signals AS generated by the differential amplification device 530 under the first and second states. The external device may calculate the difference between the amplification signals AS generated by the differential amplification device 530 under the first and second states, and then compare the calculated difference value with the data which is stored in advance. Consequently, the electric field of the measurement target is measured accurately.

When the intensity of the transmissive light TL is coincident to the intensity of the reflected light RL, a change rate of the intensity of the transmissive light TL and the reflected light RL is maximized. Since the voltage application device 610C sets a voltage as the reference voltage if the change rate of the intensity of the transmissive light TL and the reflected light RL is maximized at the voltage, the electric field measurement device 100C may measure the electric field of the measurement target accurately.

In the processing loop from step S430 to step S460, the electric field measurement element 120 functions as a reference element for obtaining a reference. In steps S480 and S490, the electric field measurement element 120 functions as a measurement element for measuring an electric field. Therefore, the electric field measurement device 100C is smaller and simpler than a conventional electric field measurement device which requires a reference element and a measurement element separate from the reference element.

The processing loop from step S430 to step S460 makes Bragg wavelength coincident to a wavelength of light propagating along the core layer 210 under various temperature conditions and various humidity conditions. Therefore, the electric field measurement device 100C may measure an electric field of a measurement target accurately under various environmental conditions.

A designer may design the electric field measurement device 100C without a spectroscopic element. Therefore, the electric field measurement device 100C may perform electric field measurement very responsively. In addition, a designer may give the electric field measurement device 100C a small structure which allows easy fabrication.

Sixth Embodiment

In the second to fifth embodiments, the electric field measurement device uses a comb-shaped pattern electrode to cause a periodic refractive index distribution. Alternatively, an electric field measurement device may have other pattern electrodes which cause a periodic refractive index distribution. A pattern electrode formed with an opening pattern which causes a periodic refractive index distribution is described in the sixth embodiment. The pattern electrode of the sixth embodiment may be used instead of the pattern electrode described in the context of the second to fifth embodiments.

Figure 13:
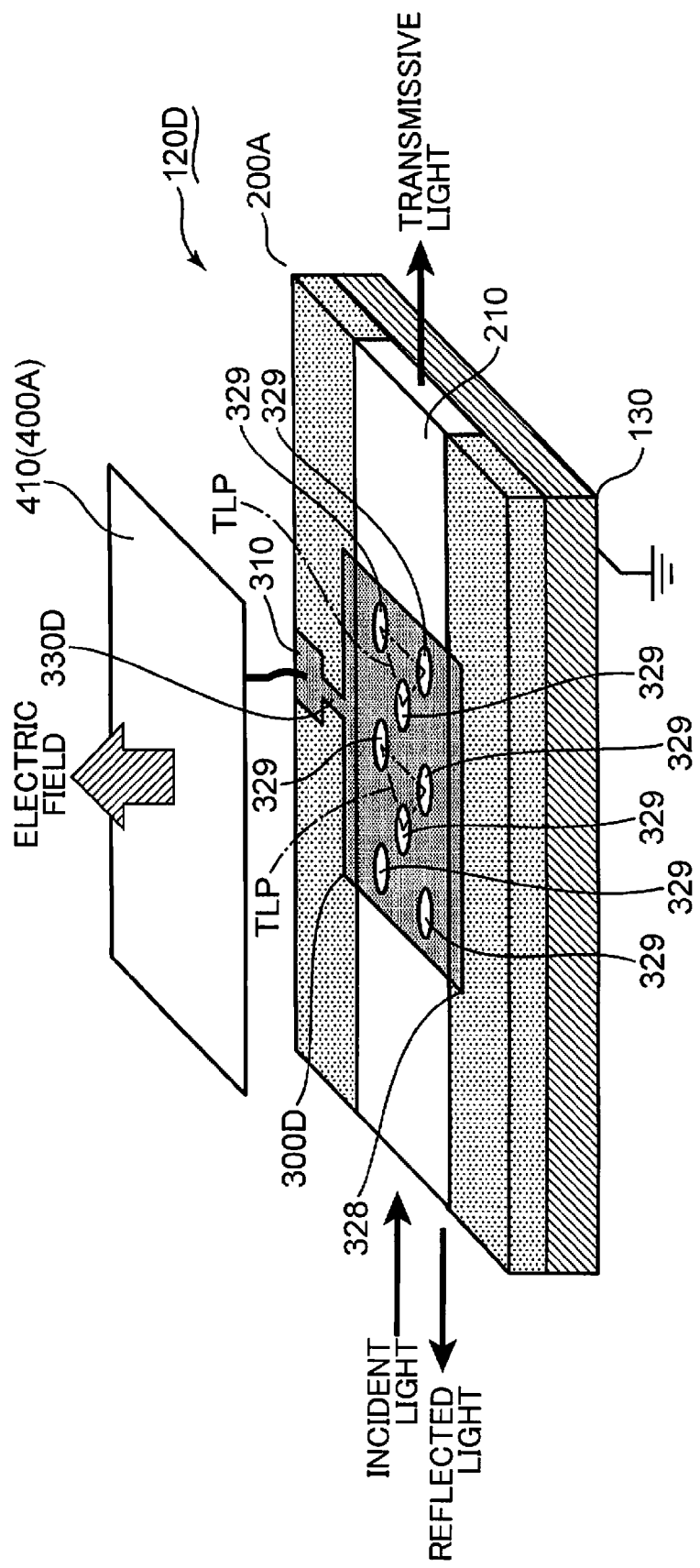
FIG. 13 is a schematic perspective view of an electric field measurement element (the sixth embodiment).

FIG. 13 is a schematic perspective view of an electric field measurement element 120D. The electric field measurement element 120D is described with reference to FIG. 13. Reference signs used commonly between the second and sixth embodiments indicate that components denoted by the common reference signs have the same functions as the second embodiment. Therefore, the description of the second embodiment is applicable to these components.

Like the second embodiment, the electric field measurement element 120D includes the substrate 130 and the optical waveguide 200A. The description of the second embodiment is applicable to these components.

The electric field measurement element 120D includes a pattern electrode 300D. The pattern electrode 300D is formed on the optical waveguide 200A.

The pattern electrode 300D includes the rectangular connection region 310. The description of the second embodiment is applicable to the connection region 310.

The pattern electrode 300D includes a main region 328 and an intermediate region 330D. The intermediate region 330D connects the main region 328 with the connection region 310. The main region 328 is formed with circular openings 329. The openings 329 form a triangular lattice patterns TLP repeated along the propagation path of light. In this embodiment, the electrode layer is exemplified by the main region 328.

When an electric field of a measurement target is applied to the metal plate 410, an induced voltage occurs in the pattern electrode 300D. Consequently, an electric field approximately orthogonal to the surface of the optical waveguide 200A, on which the pattern electrode 300A is formed, occurs between the pattern electrode 300D and the substrate 130.

Consequently, a refractive index distribution in correspondence to the shape of the main region 328 occurs in the core layer 210 of the optical waveguide 200A. In short, a high refractive index occurs in a region in which the opening 329 is formed whereas a low refractive index occurs in other regions. The refractive index distribution induced by the pattern electrode 300D functions as a reflector due to a photonic crystal. Therefore, at least a part of light propagating along the core layer 210 is reflected. Since the refractive index distribution changes in response to intensity of the electric field, a proportion of reflected light to transmissive light emitted from the core layer 210 depends on the intensity of the electric field.

If there is constant periodic variation amplitude of refractive index, which occurs under application of the electric field, a wavelength of light reflected under the presence of the refractive index distribution depends on a size of the opening 329 and a formation period of the lattice pattern TLP. Therefore, the size of the opening 329 and the formation period of the lattice pattern TLP may be determined to be suitable for a wavelength of light propagating along the core layer 210.

As described above, reflectivity and transmissivity of the core layer 210 depend on a magnitude of an electric field of a measurement target coupled to the core layer 210. Therefore, if there is measurement for intensity of at least one of reflected light and transmissive light, which are emitted from the core layer 210, the electric field of the measurement target is measured very accurately. Therefore, the principles of this embodiment do not require very accurate processes for an electro-optic crystal used as the core layer 210. Accordingly, a designer may give the electric field measurement device a small structure which allows easy fabrication.

In this embodiment, the openings 329 forming the triangular lattice patterns TLP are used. Alternatively, other opening patterns configured to give the core layer 210 a periodic refractive index distribution may be used. The principles of this embodiment are not limited to a specific opening pattern.

Like the second to fifth embodiments, the electric field measurement element 120D may function as a reference element for obtaining a reference and a measurement element for measuring an electric field. Therefore, an electric field measurement device into which the electric field measurement element 120D is incorporated becomes small and simplified.

Like the second to fifth embodiments, a designer may design an electric field measurement device, into which the electric field measurement element 120D is incorporated, without a spectroscopic element. Therefore, the electric field measurement device may measure an electric field very responsively.

Seventh Embodiment

In the second to sixth embodiments, a substrate of an electric field element functions as a ground electrode. Therefore, in the second to sixth embodiments, the substrate is formed from a conductive material. However, a substrate may be non-conductive. An electric field measurement element formed from a non-conductive substrate is described in the seventh embodiment. The electric field measurement element according to the seventh embodiment may be used instead of the electric field measurement element described in the context of the second to fifth embodiments.

Figure 14:
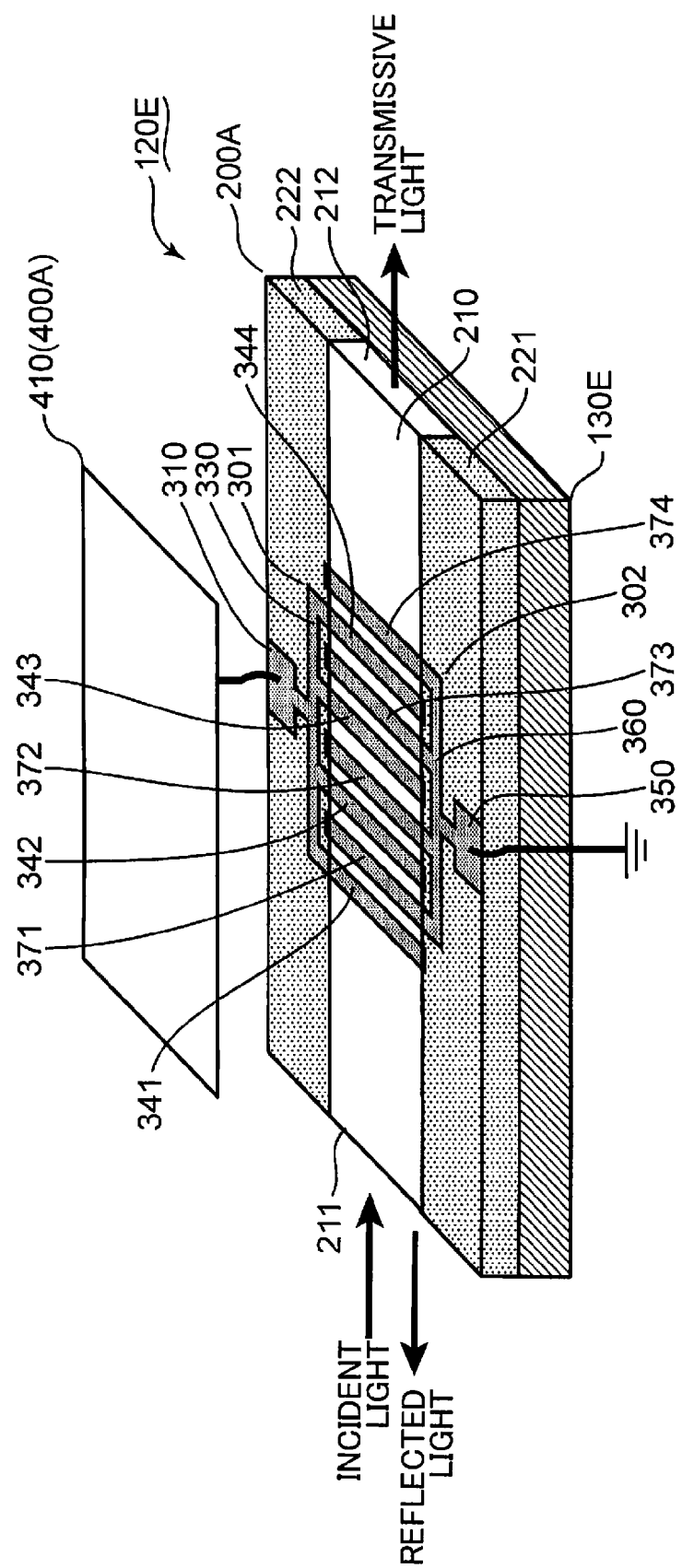
FIG. 14 is a schematic perspective view of an electric field measurement element (the seventh embodiment).

FIG. 14 is a schematic perspective view of an electric field measurement element 120E. The electric field measurement element 120E is described with reference to FIG. 14. Reference signs used commonly between the second and seventh embodiments indicate that components denoted by the common reference signs have the same functions as the second embodiment. Therefore, the description of the second embodiment is applicable to these components.

Like the second embodiment, the electric field measurement element 120E includes the optical waveguide 200A. The description of the second embodiment is applicable to the optical waveguide 200A.

The electric field measurement element 120E includes a substrate 130E, a first pattern electrode 301 and a second pattern electrode 302. The substrate 130E supports the optical waveguide 200A. The first and second pattern electrodes 301, 302 are formed on the optical waveguide 200A.

Like the pattern electrode of the second embodiment, the first pattern electrode 301 includes the rectangular connection region 310 and the substantially T-shaped intermediate region 330. The description about the pattern electrode of the second embodiment is applicable to these components.

The first pattern electrode 301 further includes strip regions 341 to 344. Each of the strip regions 341 to 344 extends from the intermediate region 330 toward the cladding layer 221 across the core layer 210. The strip regions 341 to 344 are aligned to be apart from each other at substantially regular intervals in the propagating direction of light.

The second pattern electrode 302 includes a rectangular connection region 350, a substantially T-shaped intermediate region 360 and strip regions 371 to 374. The connection region 350 is connected to the ground. Therefore, the second pattern electrode 302 may function as a ground electrode for the first pattern electrode 301. A metal larger than the substrate 130E may be used as a ground. Accordingly, an electric field is coupled appropriately from the first pattern electrode 301 to the optical waveguide 200A. Connection between the second pattern electrode 302 and the ground is not mandatory. The principles of this embodiment are not limited in any way by whether or not the second pattern electrode 302 is connected to the ground.

The intermediate region 360 connects the connection region 350 with the strip regions 371 to 374. Each of the strip regions 371 to 374 extends from the intermediate region 360 toward the cladding layer 222 across the core layer 210. The strip regions 371 to 374 are aligned to be apart from each other at substantially regular intervals in the propagating direction of light.

The strip region 371 of the second pattern electrode 302 is arranged between the strip regions 341, 342 of the first pattern electrode 301. The strip region 344 of the first pattern electrode 301 is arranged between the strip regions 373, 374 of the second pattern electrode 302.

The strip region 372 of the second pattern electrode 302 is arranged between the strip regions 342, 343 of the first pattern electrode 301. The strip region 373 of the second pattern electrode 302 is arranged between the strip regions 343, 344 of the first pattern electrode 301.

Since the second pattern electrode 302 functions as a ground electrode as described above, the substrate 130E may be not conductive. Therefore, the following materials may be utilized as the substrate 130E.

Oxide such as $Al_2O_3$, MgO, $SrTiO_3$, Al-doped ZnO, $In_2O_3$, $RuO_2$, $BaPbO_2$, $SrRuO_2$, $Mg_2TiO_4$ or $MgTi_2O_4$ Element semiconductor such as Si, Ge or diamond III-V compound semiconductor such as GaAs, GaSb, InP, InSb or AlGaAs II-VI compound semiconductor such as ZnS, ZnSe, ZnTe or CaSe Metal such as Pt, Pd, Al or Ag Electro-optic crystal having an electro-optic effect such as lithium niobate ($LiNbO_3$), lithium tantalate ($LiTaO_3$), KTN ($KTa_1$-$xNbxO_3$ where x is ranged in 0<x<1) or KTP ($KTiOPO_4$)

When a user gets the metal plate 410 of the antenna 400A closer to a measurement target, an electric field of the measurement target is applied to the metal plate 410. Consequently, an induced voltage occurs in the first pattern electrode 301 connected to the antenna 400A. Accordingly, an electric field in a direction along the propagating direction of light occurs between the first and second pattern electrodes 301, 302.

As a result of the occurrence of the electric field in the core layer 210, a periodic refractive index distribution in correspondence to the shape of the first and second pattern electrodes 301, 302 occurs in the core layer 210. In short, a high refractive index is obtained in a region in which both of the first and second pattern electrodes 301, 302 are absent whereas a low refractive index is obtained in a region in which the first or second pattern electrode 301, 302 is present. The region of a high refractive index and the region of a low refractive index are aligned alternately along the propagating direction of light.

The periodic distribution of a refractive index functions as Bragg reflector. Therefore, a part of light propagating in the optical waveguide 200A is emitted as reflected light from the first end surface 211 of the optical waveguide 200A. A wavelength of the light reflected by the periodic distribution of a refractive index is determined by Bragg wavelength. If there is constant periodic variation amplitude of a refractive index which occurs under application of the electric field, Bragg wavelength depends on a period called the grating period (i.e. structural period of the pattern electrode 300A). Therefore, a designer may determine an alignment period of the strip regions 341 to 344, 371 to 374 so that Bragg wavelength becomes substantially as long as a wavelength of light propagating along the optical waveguide 200A.

As described above, reflectivity and transmissivity of the core layer 210 depend on a magnitude of an electric field of a measurement target coupled to the core layer 210. Therefore, if there is measurement for intensity of at least one of reflected light and transmissive light which are emitted from the core layer 210, the electric field of the measurement target is measured accurately. Accordingly, the principles of this embodiment do not require very accurate processes for an electro-optic crystal used as the core layer 210. Therefore, a designer may give an electric field measurement device a small structure which allows easy fabrication.

In this embodiment, a pair of comb-shaped electrodes (the first and second pattern electrodes 301, 302) is used. Alternatively, an electrode of other shapes configured to give the core layer 210 a periodic refractive index distribution may be used. The principles of this embodiment are not limited to a specific electrode shape.

Like the second to fifth embodiments, the electric field measurement element 120E may function as a reference element for obtaining a reference and a measurement element for measuring an electric field. Therefore, an electric field measurement device into which the electric field measurement element 120E is incorporated becomes small and simplified.

Like the second to fifth embodiments, a designer may design an electric field measurement device, into which the electric field measurement element 120E is incorporated, without a spectroscopic element. Therefore, the electric field measurement device may measure an electric field very responsively.

The principles of the aforementioned various embodiments may be combined appropriately in accordance with an application of the electric field measurement device.

The techniques about the exemplary electric field measurement devices described in the context of the aforementioned various embodiments mainly include the following features.

An electric field measurement device according to one aspect of the aforementioned embodiments measures an electric field of a measurement target. The electric field measurement device includes an optical waveguide configured to transmit transmission light, an electrode portion configured to give optical characteristics of the optical waveguide a periodic variation, an antenna configured to set a first state, in which the electric field is coupled to the optical waveguide, and a second state, in which the electric field is disconnected from the optical waveguide, a detector configured to detect light intensity of emission light emitted from the optical waveguide, and an applicator which applies a voltage to the electrode portion to give the periodic variation. The applicator includes a setting portion, which sets a reference voltage in correspondence to the light intensity under the second state, and an output portion, which outputs a voltage in correspondence to a difference between the reference voltage and an induced voltage happening to the electrode portion under the first state.

According to the aforementioned configuration, the magnitude of the reference voltage corresponds to an environment in which the electric field is measured since the setting portion sets the reference voltage in correspondence to the light intensity under the second state, in which the electric field is disconnected from the optical waveguide. Since the output portion outputs a voltage in correspondence to a difference between the reference voltage and the induced voltage happening to the electrode portion under the first state, in which the electric field is coupled to the optical waveguide, the electric field measurement device may detect an electric field accurately even under an environmental change.

In the aforementioned configuration, the electrode portion may cause a periodic variation of a refractive index in the optical waveguide as the periodic variation of the optical characteristics.

According to the aforementioned configuration, the electric field measurement device may detect an electric field accurately even under an environmental change since the electrode portion causes a periodic variation of the refractive index in the optical waveguide as the periodic variation of the optical characteristics.

In the aforementioned configuration, the emission light may include at least one of transmissive light, which passes through the optical waveguide, and reflected light, which is reflected in the optical waveguide.

According to the aforementioned configuration, the electric field measurement device may detect the electric field accurately from at least one of the transmissive light and the reflected light since the emission light includes at least one of the transmissive light, which passes through the optical waveguide, and the reflected light, which is reflected in the optical waveguide.

In the aforementioned configuration, the electrode portion may be situated between the antenna and the optical waveguide.

According to the aforementioned configuration, the electric field measurement device may appropriately couple an electric field to the optical waveguide under the first state since the electrode portion is situated between the antenna and the optical waveguide. Accordingly, the electric field measurement device may measure the electric field accurately.

In the aforementioned configuration, the optical waveguide may be formed from an electro-optic crystal.

According to the aforementioned configuration, the electric field measurement device may be responsive since the optical waveguide is formed from an electro-optic crystal.

In the aforementioned configuration, a composition of the electro-optic crystal may be $KTa_{1-x}Nb_xO_3$ (where x is ranged in $0<x<1$).

According to the aforementioned configuration, the electric field measurement device may respond very sensitively since the composition of the electro-optic crystal is $KTa_{1-x}Nb_xO_3$ (where x is ranged in $0<x<1$).

In the aforementioned configuration, reflectivity of the optical waveguide may be maximized when the reference voltage is applied to the optical waveguide under the second state.

According to the aforementioned configuration, the reference voltage is set appropriately.

In the aforementioned configuration, the detector may include a first photo-detector, which converts intensity of the transmissive light to a first electrical signal, a second photo-detector, which converts intensity of the reflected light to a second electrical signal, and an amplifier, which amplifies a difference between the first and second electrical signals to generate an amplification signal. The setting portion may set the reference voltage in response to the amplification signal.

According to the aforementioned configuration, the reference voltage is set appropriately.

In the aforementioned configuration, a change in reflectivity of the optical waveguide may be maximized when the reference voltage is applied to the optical waveguide under the second state.

According to the aforementioned configuration, the reference voltage is set appropriately.

In the aforementioned configuration, a difference between reflectivity and transmissivity of the optical waveguide may be minimized when the reference voltage is applied to the optical waveguide under the second state.

According to the aforementioned configuration, the reference voltage is set appropriately.

In the aforementioned configuration, the electrode portion may include a first electrode extending in a direction intersecting with a transmission direction, in which the transmission light is transmitted, and a second electrode apart from the first electrode in the transmission direction.

According to the aforementioned configuration, the electrode portion may give the optical characteristics of the optical waveguide the periodic variation since the electrode portion includes the first electrode extending in a direction intersecting with the transmission direction, in which the transmission light is transmitted, and the second electrode apart from the first electrode in the transmission direction.

In the aforementioned configuration, the electrode portion may include a third electrode apart from the second electrode in the transmission direction. The second electrode may be arranged in an intermediate position between the first and third electrodes.

According to the aforementioned configuration, the electrode portion may give the optical characteristics of the optical waveguide the periodic variation since the second electrode is arranged in an intermediate position between the first and third electrodes.

In the aforementioned configuration, the electrode portion may include an electrode layer formed with an opening pattern repeating periodically in a transmission direction in which the transmission light is transmitted.

According to the aforementioned configuration, the electrode portion may give the optical characteristics of the optical waveguide the periodic variation since the electrode portion includes the electrode layer formed with the opening pattern repeating periodically in the transmission direction, in which the transmission light is transmitted.

In the aforementioned configuration, the electric field measurement device may further include a light source portion configured to emit incident light, which enters the optical waveguide and becomes the transmission light. The light source portion may include at least one of a light-emitting diode and a laser source.

According to the aforementioned configuration, the electric field measurement device may detect an electric field accurately even under an environmental change since the light source portion includes at least one of a light-emitting diode and an laser source.

INDUSTRIAL APPLICABILITY

The principles of the aforementioned embodiment are applicable to various devices which require measurement of an electric field. For example, a designer may design a human body communication device configured to perform data communication between wearable computers on the basis of the principles of the aforementioned embodiments. Another designer may design an electric field detection-type electroencephalograph on the basis of the principles of the aforementioned embodiments.

The invention claimed is:

1. An electric field measurement device for measuring an electric field of a measurement target, comprising:
   an optical waveguide configured to transmit transmission light;
   an electrode portion configured to give optical characteristics of the optical waveguide a periodic variation;
   an antenna configured to set a first state, in which the electric field is coupled to the optical waveguide, and a second state, in which the electric field is disconnected from the optical waveguide;
   a detector configured to detect light intensity of emission light emitted from the optical waveguide; and
   an applicator which applies a voltage to the electrode portion to give the periodic variation,
   wherein the applicator includes a setting portion, which sets a reference voltage in correspondence to the light intensity under the second state, and an output portion, which outputs a voltage in correspondence to a difference between the reference voltage and an induced voltage happening to the electrode portion under the first state.

2. The electric field measurement device according to claim 1,
   wherein the electrode portion causes a periodic variation of a refractive index in the optical waveguide as the periodic variation of the optical characteristics.

3. The electric field measurement device according to claim 1,
   wherein the emission light includes at least one of transmissive light, which passes through the optical waveguide, and reflected light, which is reflected in the optical waveguide.

4. The electric field measurement device according to claim 1,
   wherein the electrode portion is situated between the antenna and the optical waveguide.

5. The electric field measurement device according to claim 1,
   wherein the optical waveguide is formed from an electro-optic crystal.

6. The electric field measurement device according to claim 5,
   wherein a composition of the electro-optic crystal is $KTa_{1-x}Nb_xO_3$ (where x is ranged in $0<x<1$).

7. The electric field measurement device according to claim 1,
   wherein reflectivity of the optical waveguide has a larger value under application of the reference voltage than under application of another voltage during the second state.

8. The electric field measurement device according to claim 3,
   wherein the detector includes a first photo-detector, which converts intensity of the transmissive light into a first electrical signal, a second photo-detector, which converts intensity of the reflected light into a second electrical signal, and an amplifier, which amplifies a difference between the first and second electrical signals to generate an amplification signal, and
   wherein the setting portion sets the reference voltage in response to the amplification signal.

9. The electric field measurement device according to claim 8,
   wherein a change in reflectivity of the optical waveguide has a larger value under application of the reference voltage than under application of another voltage during the second state.

10. The electric field measurement device according to claim 8,
    wherein a difference between reflectivity and transmissivity of the optical waveguide has a smaller value under application of the reference voltage than under application of another voltage during the second state.

11. The electric field measurement device according to claim 1,
    wherein the electrode portion includes a first electrode extending in a direction intersecting with a transmission direction, in which the transmission light is transmitted, and a second electrode, which is apart from the first electrode in the transmission direction.

12. The electric field measurement device according to claim 11,
wherein the electrode portion includes a third electrode, which is apart from the second electrode in the transmission direction, and
wherein the second electrode is situated in an intermediate position between the first and third electrodes.

13. The electric field measurement device according to claim 1,
wherein the electrode portion includes an electrode layer formed with an opening pattern repeating periodically in a transmission direction in which the transmission light is transmitted.

14. The electric field measurement device according to claim 1, further comprising:
a light source portion configured to emit incident light, which enters the optical waveguide and becomes the transmission light,
wherein the light source portion includes at least one of a light-emitting diode and a laser source.

* * * * *